United States Patent
Gau et al.

(10) Patent No.: US 7,476,360 B2
(45) Date of Patent: Jan. 13, 2009

(54) CARTRIDGE FOR USE WITH ELECTROCHEMICAL SENSOR

(75) Inventors: Jen-Jr Gau, Pasadena, CA (US); Arvin Trung Chang, West Covina, CA (US)

(73) Assignee: Genefluidics, Inc., Monterey Park, CA (US)

( * ) Notice: Subject to any disclaimer, the term of this patent is extended or adjusted under 35 U.S.C. 154(b) by 604 days.

(21) Appl. No.: 10/941,517

(22) Filed: Sep. 14, 2004

(65) Prior Publication Data

US 2005/0196855 A1    Sep. 8, 2005

Related U.S. Application Data

(60) Provisional application No. 60/528,566, filed on Dec. 9, 2003.

(51) Int. Cl.
    *G01N 33/00*    (2006.01)
(52) U.S. Cl. .................. 422/58; 422/50; 422/68.1; 422/99; 422/100; 422/102; 422/104
(58) Field of Classification Search .................. 422/58, 422/50, 68.1, 99, 100, 102, 104
    See application file for complete search history.

(56) References Cited

U.S. PATENT DOCUMENTS

| | | | |
|---|---|---|---|
| 4,323,536 A | 4/1982 | Columbus | |
| 4,399,225 A | 8/1983 | Hansen et al. | |
| 4,426,451 A | 1/1984 | Columbus | |
| 5,096,669 A * | 3/1992 | Lauks et al. | 204/403.02 |
| 5,296,123 A | 3/1994 | Reddy et al. | |
| 5,571,410 A | 11/1996 | Swedberg et al. | |
| 5,726,013 A * | 3/1998 | Clark | 435/5 |
| 5,932,799 A | 8/1999 | Moles | |
| 5,972,199 A | 10/1999 | Heller et al. | |
| 5,980,704 A | 11/1999 | Cherukuri et al. | |
| 6,030,581 A | 2/2000 | Virtanen | |
| 6,117,290 A | 9/2000 | Say et al. | |
| 6,167,910 B1 | 1/2001 | Chow | |
| 6,251,343 B1 | 6/2001 | Dubrow et al. | |
| 6,331,439 B1 | 12/2001 | Cherukuri et al. | |
| 6,440,725 B1 | 8/2002 | Pourahmadi et al. | |
| 6,454,924 B2 | 9/2002 | Jedrzejewski et al. | |
| 6,498,353 B2 | 12/2002 | Nagle et al. | |
| 6,582,963 B1 | 6/2003 | Weigl et al. | |
| 6,632,619 B1 | 10/2003 | Harrison et al. | |
| 6,670,115 B1 | 12/2003 | Zhang | |

* cited by examiner

*Primary Examiner*—Sam P Siefke
(74) *Attorney, Agent, or Firm*—Gavrilovich, Dodd & Lindsey, LLP

(57) ABSTRACT

A cartridge is disclosed. The cartridge includes an independent storage component and transport component. The storage component can be coupled with the transport component. The storage component includes one or more pockets that each contain a solution to be used in an assay. The transport component is configured to transport the solutions from the pockets of the storage component to a sensor positioned in the transport component.

61 Claims, 14 Drawing Sheets

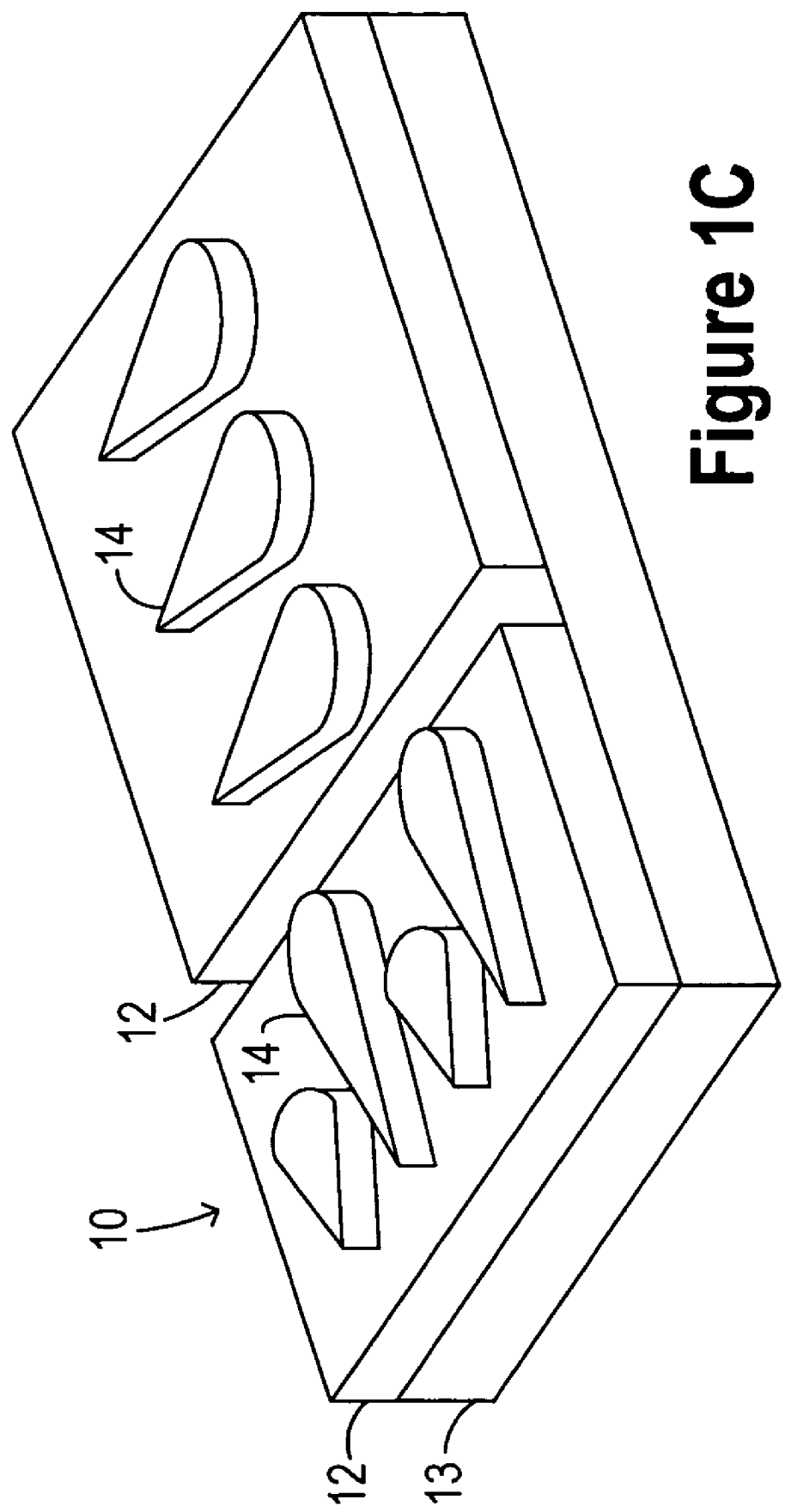

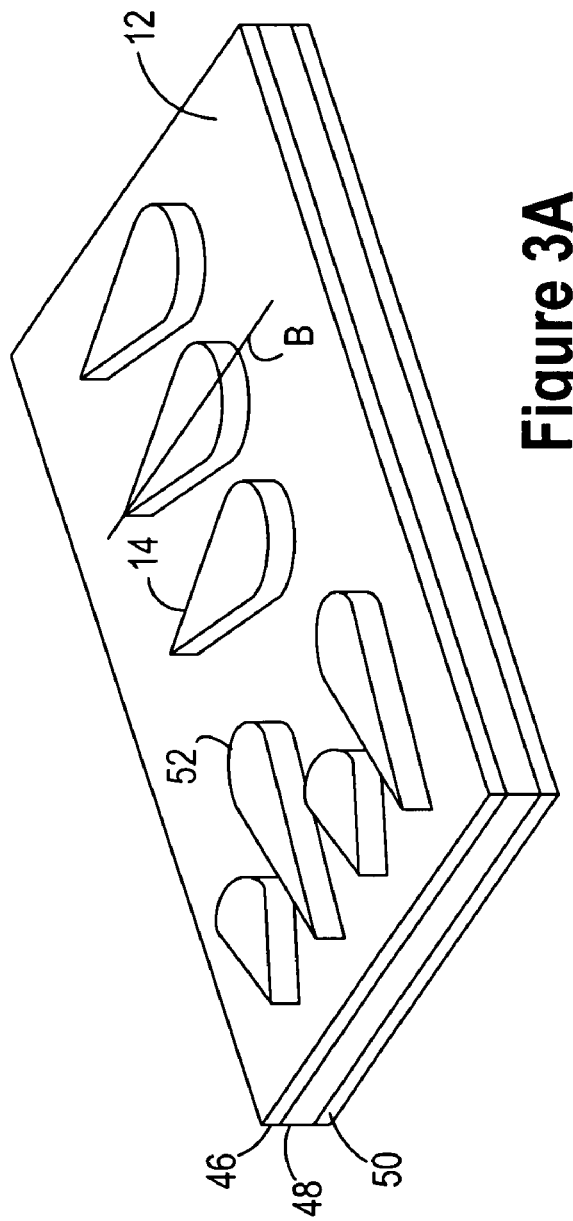
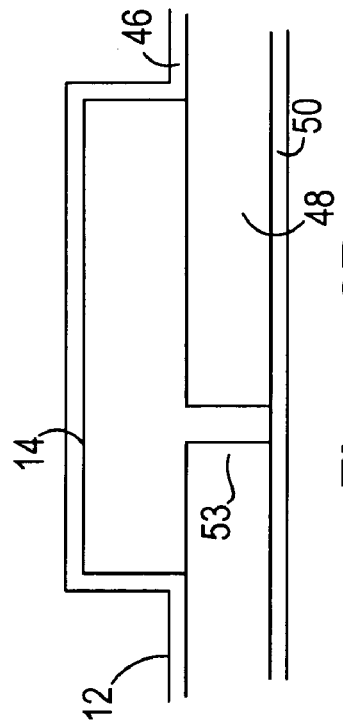

CARTRIDGE FOR USE WITH ELECTROCHEMICAL SENSOR

RELATED APPLICATIONS

This application claims priority to U.S. Provisional Patent Application Ser. No. 60/528,566; filed on Dec. 9, 2003; entitled "Cartridge for Use With Electrochemical Sensors" and incorporated herein in its entirety.

BACKGROUND

1. Field of the Invention

The invention relates to assays and more particular to a cartridge for use with assays.

2. Background of the Invention

A variety of assays have been developed to detect the presence and/or amount of biological or chemical agents in a sample. The desire for assays that can be performed in the field has increased the demand for smaller and more efficient assay equipment. This demand has been met with equipment that employs one or more sensors held within a cartridge. The cartridge can generally be extracted from or inserted into an assay system at the location where the assay is performed.

During an assay, one or more solutions are delivered to the sensors. The storage and preparation of these solutions is a significant obstacles to the implementation of the technologies. An additional obstacle is the difficulty associated with effectively transporting these solutions to the sensor under the proper conditions. As a result, there is a need for more efficient and effective assay equipment.

SUMMARY OF THE INVENTION

A cartridge is disclosed. The cartridge includes an independent storage component and transport component. The storage component can be removably attached to the transport component. The storage component includes one or more reservoirs that each contain a solution to be used in an assay. The transport component is configured to transport the solutions from the reservoirs of the storage component to a sensor positioned in the transport component. In some instances, a plurality of storage components are configured to be concurrently coupled with the transport component.

The transport component can include one or more disruption mechanisms configured to disrupt the sealing integrity of a material on the storage component upon coupling of the transport component and the storage component. The disruption mechanisms can disrupt the sealing integrity so as to provide an outlet through which a solution in a reservoir can flow out of the storage component. One or more of the disruption mechanisms includes a piercing mechanism configured to pierce the material. One or more of the disruption mechanisms can include a stretching mechanism configured to stretch the material such that one or more channels in the material open up.

The transport component can include a vent channel, an input channel and an output channel meeting at a valve. The valve is configured to control flow of a solution from the input channel to the output channel while venting gasses into the vent channel. In some instances, the component includes an obstruction positioned between the input channel and the output channel and a flexible material positioned over the obstruction. The flexible materials can be positioned such that the displacement between the obstruction and the flexible material changes during operation of the valve.

Another embodiment of the transport component is disclosed. The transport component includes a valve configured to control flow of a solution around an obstruction positioned between an input channel and an output channel. The valve includes a flexible material positioned over the obstruction such that a displacement between the obstruction and the flexible material changes during operation of the valve. A portion of the input channel slopes toward the flexible material when moving along the input channel toward the valve.

Methods of using the cartridge, the transport component and the storage component are also disclosed.

BRIEF DESCRIPTION OF THE FIGURES

FIG. 1A through FIG. 1C illustrate a cartridge for use with an electrochemical sensor. The cartridge includes a storage component configured to be coupled with a transport component. FIG. 1A is a perspective view of a storage component and a transport component before assembly of the cartridge.

FIG. 1B is a perspective view of the cartridge after assembly.

FIG. 1C is a perspective view of a cartridge having two storage components that are each coupled with a transport component.

FIG. 3A through FIG. 3C illustrate a suitable construction for a storage component. FIG. 3A is a perspective view of the storage component. The storage component includes a cover, a base, and a sealing medium.

FIG. 3B is a cross section of the storage component shown in FIG. 3A taken along the line labeled B.

FIG. 3C is a perspective view of the storage component before assembly of the storage component.

FIG. 4A is a cross section of the storage component shown in FIG. 3A taken along the line labeled B.

FIG. 4B is a bottom view of the storage component shown in FIG. 4A without the sealing medium in place.

FIG. 4C is a perspective view of a portion of the transport component.

FIG. 4D is a cross section of a cartridge employing the disruption mechanism illustrated on the transport component of FIG. 4C.

FIG. 5A is a perspective view of the parts of a transport component before assembly of the transport component.

FIG. 5B is a different perspective view of the parts of a transport component before assembly of the transport component. The view of FIG. 5B is inverted relative to the view of FIG. 5A.

FIG. 5C is a cross section of the cover shown in FIG. 5B taken along the line labeled C.

FIG. 5D is a cross section of a portion of the transport component having a vent channel.

FIG. 5E is bottom view of the portion of a cover having a vent channel with a constriction region.

FIG. 5F is a cross section of the constriction region taken at the line labeled F.

FIG. 6A is a topview of the portion of the transport component that includes the valve.

FIG. 6B is a bottom view of the portion of the transport component shown in FIG. 6A.

FIG. 6C is a cross section of the cartridge shown in FIG. 6A taken along a line extending between the brackets labeled C. The cross section shows the valve before the flow of a solution through the valve.

FIG. 6D is a cross section of the cartridge shown in FIG. 6A taken along a line extending between the brackets labeled D. The valve is shown before the flow of a solution through the valve.

FIG. 6E illustrates the valve of FIG. 6C and FIG. 6D during the flow of a solution through the valve.

FIG. 7A is a perspective view of the portion of the cover that includes the valve.

FIG. 7B illustrates a cross section of a transport component that includes the cover shown in FIG. 7A taken along a line extending between the brackets labeled B. The cross section illustrates a valve before the flow of a solution through the valve.

FIG. 7C illustrates a cross section of a transport component that includes the cover shown in FIG. 7A taken along a line extending between the brackets labeled C. The cross section illustrates a valve before the flow of a solution through the valve.

FIG. 7D illustrates the valve during the flow of a solution through the valve.

FIG. 8A is a sideview of a system including the cartridge positioned on a manifold.

FIG. 8B is a cross section of the system shown in FIG. 8A.

DETAILED DESCRIPTION OF THE PREFERRED EMBODIMENT

A cartridge having a storage component and a transport component is disclosed. The storage component and the transport component are independent but can be coupled with one another before and during the operation of the cartridge. The storage component includes one or more reservoirs that each contain a solution to be used in an assay. The transport component is configured to transport the solutions from the reservoirs of the storage component to a sensor positioned in the transport component. Different storage components can be sequentially used with a single transport component during a single assay or during sequentially performed assays. As a result, a plurality of storage components having the same solutions can be prepared and stored in the event that an assay is performed frequently. Alternately or additionally, a plurality of storage components having different solutions can be prepared and stored so different assays can be efficiently performed as they are needed. Accordingly, the storage components provide a simple and efficient device for storing the solutions to be used in an assay.

In some instances, a plurality of storage components can be concurrently used with a single transport component. Because different storage components can be prepared differently before being used concurrently, different storage components can be used under different conditions. For instance, one of the storage components can be heated while another of the storage components is refrigerated or at room temperature. As a result, one of the storage components coupled with a transport component can hold solutions that are heated while another storage components coupled with the same transport component can hold solutions that are refrigerated or at room temperature. Accordingly, different solutions can be transported to the sensor at different temperatures. The ability to employ solutions at different temperatures is an advantage because many assays require the use of one or more solutions at different temperatures in order to be effective.

Figure 1A:
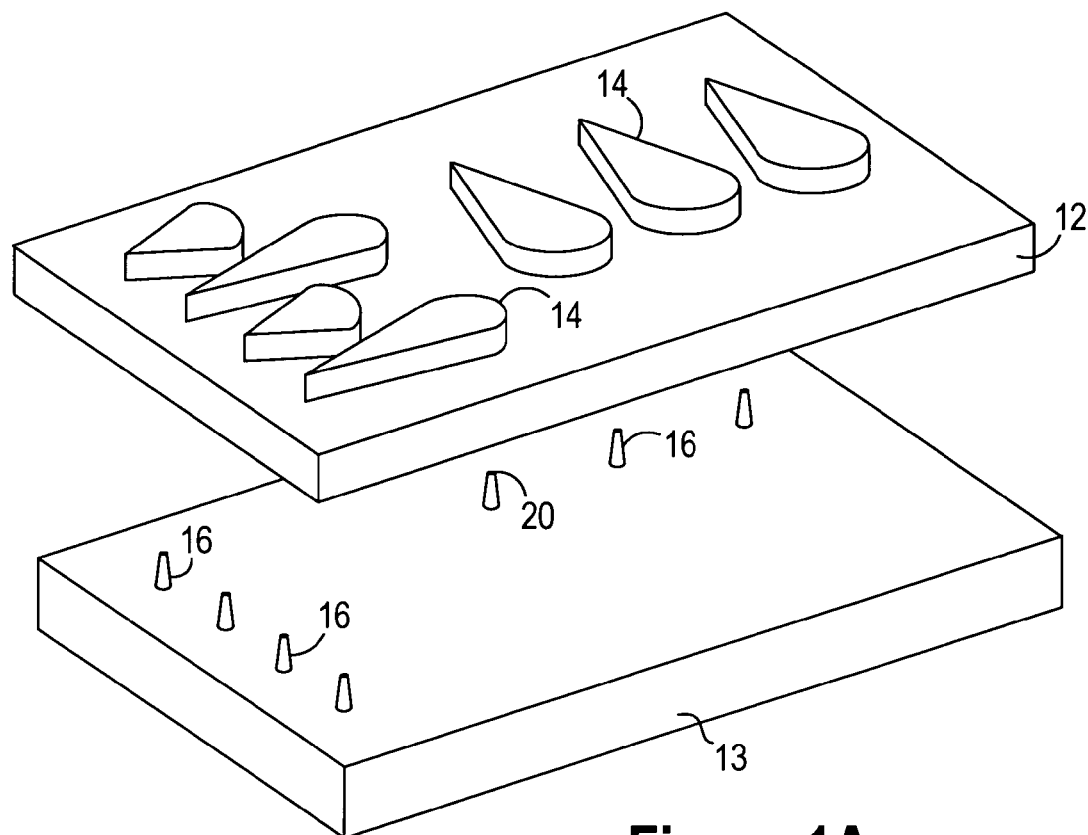
Figure 1B:
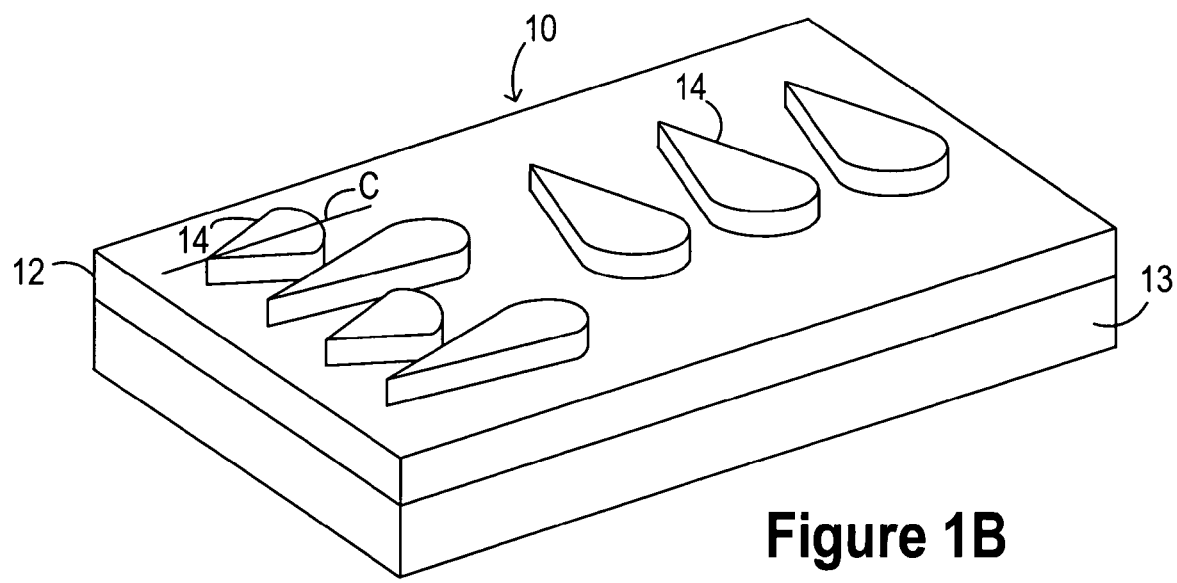

FIG. 1A through FIG. 1B illustrate a cartridge 10 for use with an electrochemical sensor. The cartridge 10 includes a storage component 12 configured to be coupled with a transport component 13. FIG. 1A is a perspective view of a storage component 12 and a transport component 13 before assembly of the cartridge 10. FIG. 1B is a perspective view of the cartridge 10 after assembly.

The storage component 12 and the transport component 13 can be coupled together so as to form a substantially planar interface. For instance, coupling the storage component 12 and the transport component 13 can place an upper side of the transport component into contact with a lower side of the storage component as evident in FIG. 1B.

The storage component 12 includes one or more reservoirs 14 configured to store solutions that are use in conjunction with an assay. The storage component can include a medium positioned so as to retain a solution in one or more of the reservoirs. In some instances, the medium is positioned so as to seal one or more of the reservoirs.

The transport component 13 is configured to transport the solutions stored in the reservoirs 14 of a storage component 12 to one or more electrochemical sensors (not shown) positioned in the transport component 13. The transport component 13 can include one or more disruption mechanisms 16 configured to disrupt the integrity of a medium on the storage component 12 so as to provide an outlet through which a solution in a reservoir 14 on the storage component can flow out of the reservoir 14 and into the transport component 13. The disruption mechanisms 16 can be configured to disrupt the integrity of the medium upon coupling of the storage component 12 to the transport component 13. In some instances, one or more of the disruption mechanisms 16 extend from a side of the transport component 13 as evident in FIG. 1A. As will become evident below, the transport mechanism 13 can also include a lumen (not shown) positioned to receive the solution flowing through the disruption provide by a disruption mechanism 16. The lumen can transport the solution into the transport mechanism 13. In some instances, the lumen is included in the disruption mechanism 16.

The cartridge can include a plurality of storage components 12. For instance, FIG. 1C is a perspective view of a cartridge 10 having two storage components 12 that are each coupled with a transport component 13. The solution(s) stored in different storage components 12 can be delivered into the transport component 13. Different storage components 12 can be treated differently before being coupled with the transport component 13. For instance, one of the storage component 12 can be left at room temperature while another storage component 12 can be refrigerated or heated. As a result, solutions from different storage components 12 can be delivered into a transport component 13 under different conditions. As an example, solutions from one storage component 12 can be delivered into the transport component 13 at room temperature while solutions from another storage component 12 can be delivered into the transport component 13 at an elevated temperature or at a reduced temperature. Accordingly, the use of multiple storage components 12 with a single transport component 13 enhances the flexibility of the cartridge 10.

Figure 2:
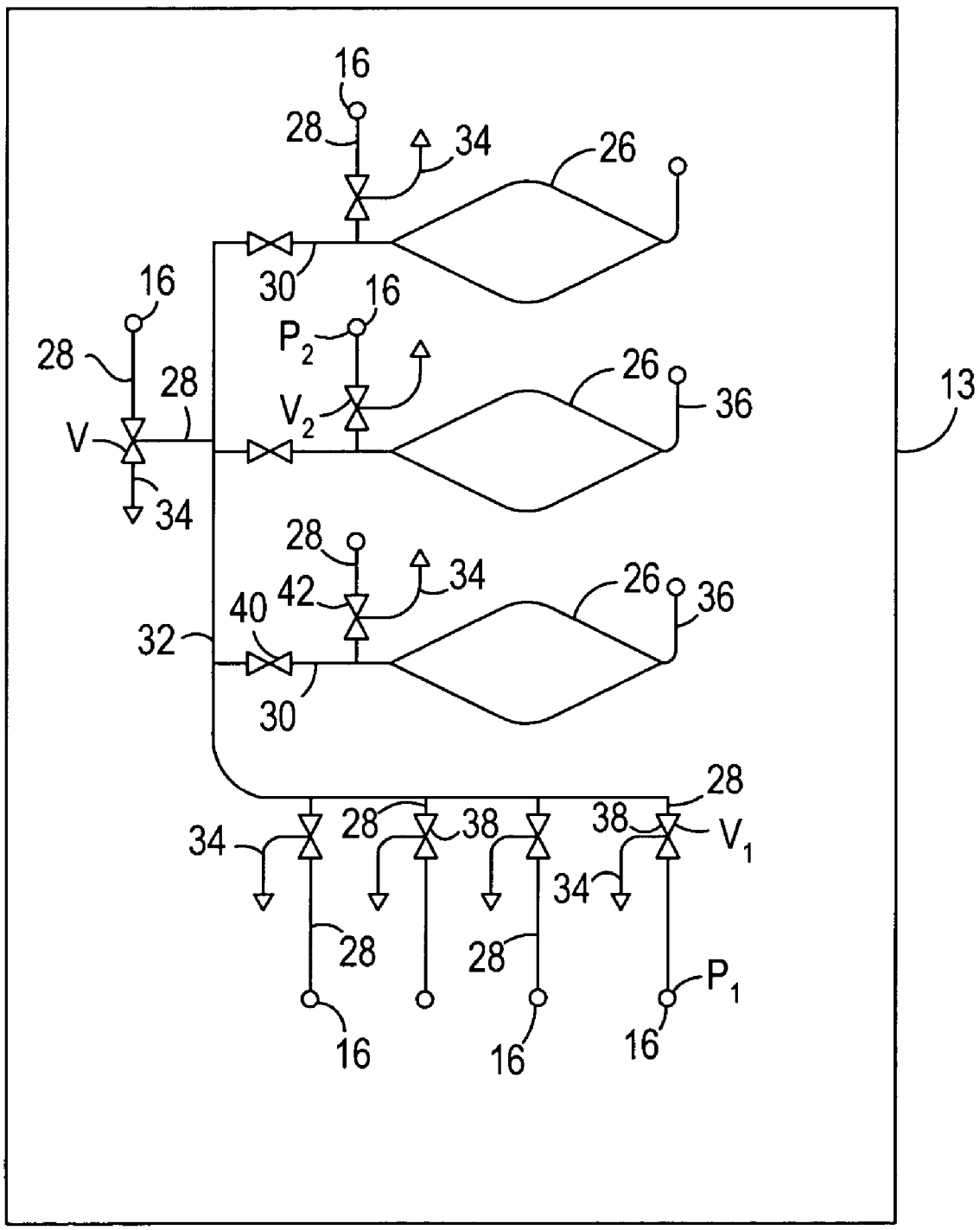
FIG. 2 is a schematic diagram illustrating the interior of the transport component.

FIG. 2 is a schematic diagram illustrating the interior of the transport component 13. The transport component 13 includes one or more sensor chambers 26. Each sensor chamber 26 is configured to hold a sensor (not shown). A suitable sensor includes, but is not limited to, an electrochemical sensor. Examples of an electrochemical sensor are taught in U.S. patent application Ser. No. 09/848,727, filed on May 5, 2001, entitled "Biological Identification System with Integrated Sensor Chip" and incorporated herein in its entirety.

The transport component 13 also includes a plurality of channels through which the solutions flow. The transport component 13 includes a plurality of inlet channels 28 that each transport fluid from a disruption mechanism 16. The transport component 13 also includes a plurality of independent channels 30 that each transport a solution to a sensor chamber 26. The transport component 13 also includes a common channel 32 that transports solutions from an inlet channel 28 to a plurality of the independent channels 30. The transport component 13 includes a waste channel 36 extending from each sensor chamber 26. The waste channel 36 is configured to carry solution away from the sensor chamber 26.

The transport component 13 includes a plurality of valves configured to control the flow of the solutions through the transport component 13. First valves 38 are each positioned between the common channel 32 and a disruption mechanism 16. Although the first valves are each shown positioned part way along the length of an inlet channel, one or more of the first valves can be positioned at the intersection of an inlet channel 28 and a common channel 32. Second valves 40 are positioned between each of the independent channels 30 and a disruption mechanism 16. Although the second valves 40 are each shown positioned part way along the length of an inlet channels 28, one or more of the first valves can be positioned at the intersection of an inlet channel 28 and an independent channel 30. Third valves 42 are positioned along the independent channels 30. Although the third valves 40 are each shown positioned part way along the length of an independent channel 30, one or more of the third valves can be positioned at an intersection of an independent channel 30 and a common channel 32.

The transport component 13 includes a plurality of vent channels 34 that each extend from a valve. Each vent channels 34 is configured to vent air from the valve while allowing solution to flow through the valve. For instance, a vent channel can be configured to vent air from an inlet channel while a solution is transported along the inlet channel and into the valve.

In some instances, a solution is transported from one of the reservoirs 14 into each of the sensor chambers 26. For instance, the pressure on a solution contained within a reservoir (not shown) disrupted by the disruption mechanism 16 labeled $P_1$ can be increased and the first valve 38 labeled $V_1$ can be opened. The solution flows through a first portion of the inlet channel 28, through the valve, into a second portion of the inlet channel and into the common channel 32. The solution flows along the common channel 32 and into contact with the third valves 40. The third valves 40 associated with the sensor chambers that are to receive the solution are opened and the solution flows through each the associated independent channels 30 and into the sensor chambers 26.

In some instances, a solution is transported from one of the reservoirs 14 into one of the sensor chambers 26. For instance, the pressure on a solution contained within a reservoir (not shown) having a seal disrupted by the disruption mechanism labeled $P_2$ can be increased and the third valve 42 labeled $V_2$ can be opened. The solution flows through a first portion of the inlet channel 28, through the valve, through a second portion of the inlet channel and into the independent channel 30. The third valve 40 at the end of the independent channel 30 remains closed and prevents the solution from flowing into the common channel 32. As a result, the solution flows through the independent channel 30 and into the sensor chamber 26.

Figure 3C:
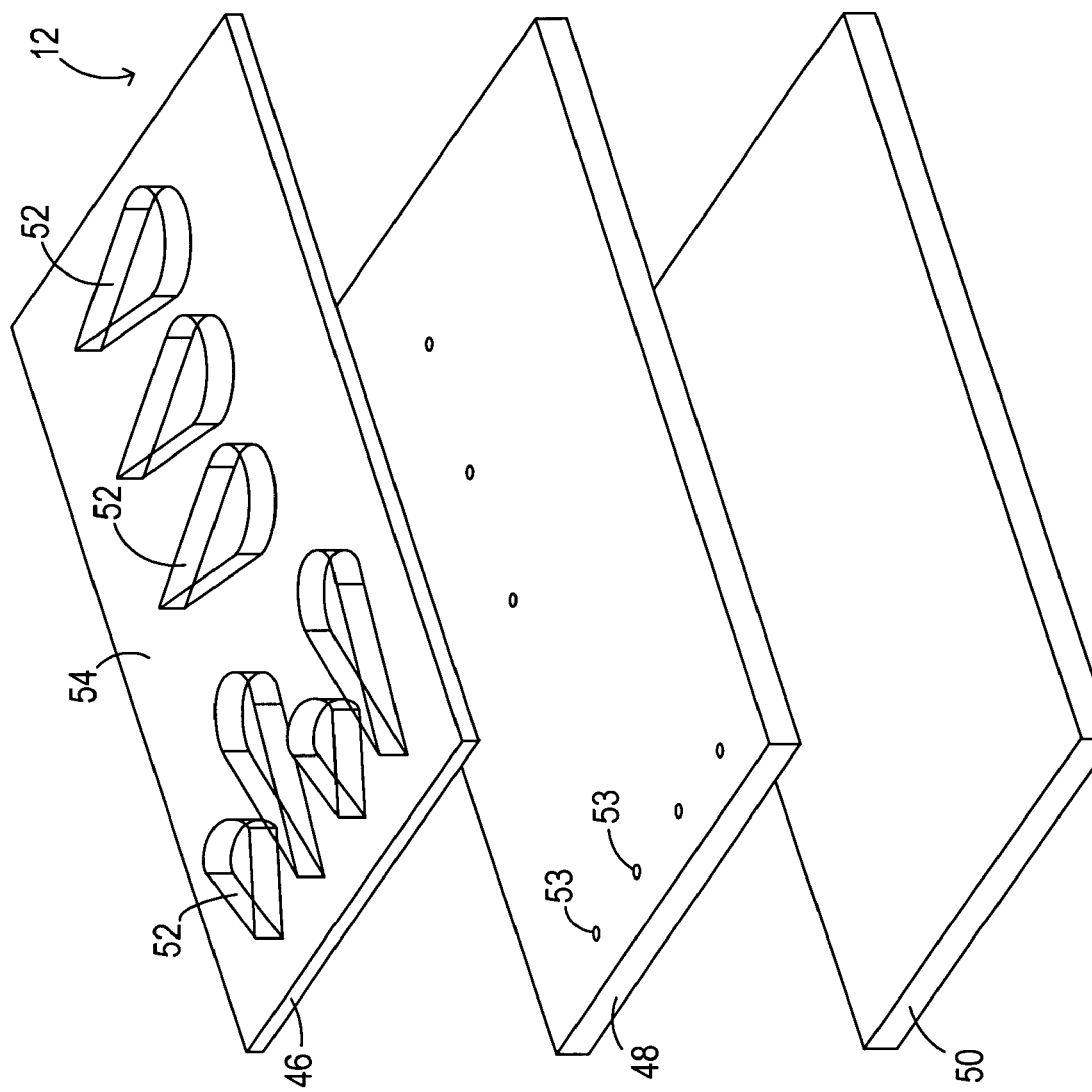

FIG. 3A through FIG. 3C illustrate a suitable construction for a storage component 12. FIG. 3A is a perspective view of the storage component 12. FIG. 3B is a cross section of the storage component 12 shown in FIG. 3A taken along the line labeled B. FIG. 3C is a perspective view of the storage component 12 before assembly of the cartridge. The storage component 12 includes a cover 46, a base 48 and a sealing medium 50. The cover 46 includes a plurality of pockets 52 extending from a common platform 54. The cover 46 is coupled with the base 48 such that the pockets 52 each define a portion of a reservoir 14 and the base 48 defines another portion of the reservoir 14. A plurality of openings 53 each extend through the base 48 and are positioned so as to provide an opening into a reservoir 14.

The sealing medium 50 extends across the holes so as to seal solutions in the reservoirs. The sealing medium 50 can include one or more layers of material. A preferred sealing medium 50 includes a primary layer that seals the openings 53 in the base 48 and can re-seal after being pierced. For instance, the sealing layer 50 can include a septum. The use of a septum can simplify the process of filling the reservoirs 14 with solution. For instance, a needle having two lumens can be inserted into a reservoir 14 through the septum and through one of the openings 53 in the base 48. The air in the reservoir 14 can be extracted from the reservoir 14 through one of the lumens and a solution can be dispensed into the reservoir 14 through the other lumen. The septum reseals after the needle is withdrawn from the reservoir 14.

A suitable material for the cover 46 includes, but is not limited to, a thermoformed film such as a thermoformed PVC film or polyurethane. The base 48 can be constructed of a rigid material. The rigid material can preserve the shape of the solution storage component. A suitable material for the base 48 includes, but is not limited to, PVC or polyurethane. A suitable material for the primary layer of the sealing medium includes, but is not limited to, septa materials such as Silicone 40D. Suitable techniques for bonding the cover to the base 48 include, but are not limited to, RF sealing. Suitable techniques for bonding the sealing medium 50 to the base 48 include, but are not limited to, laser welding, epoxies or adhesive(s).

Figure 3D:
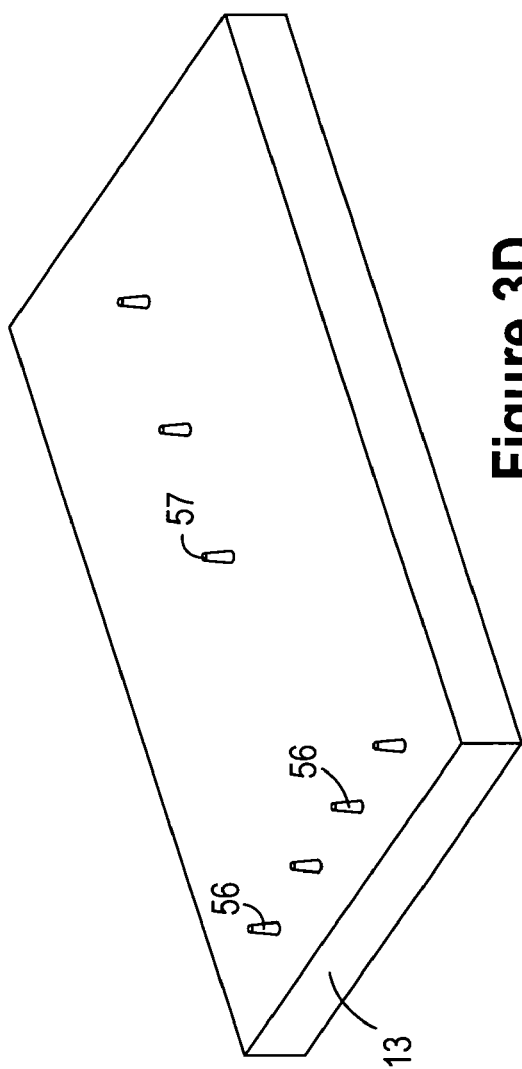
FIG. 3D is a perspective view of a transport component having disruption mechanisms suitable for use with a storage component according to FIG. 3A through FIG. 3C.
Figure 3E:
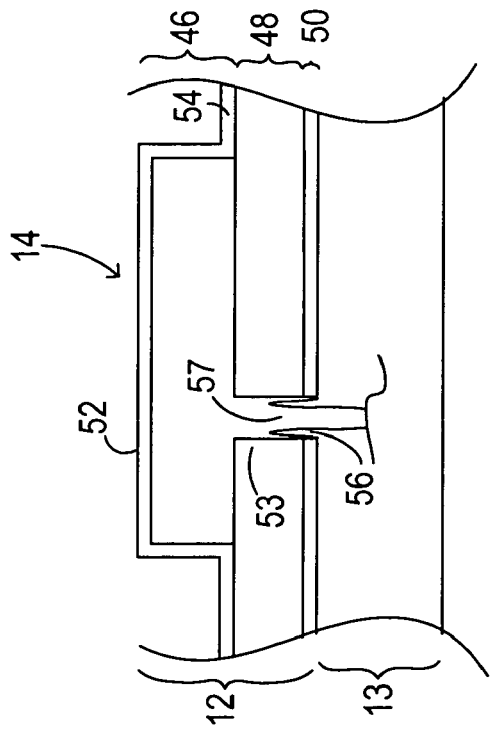
FIG. 3E is a cross section of a cartridge employing the storage component of FIG. 3A and the transport component of FIG. 3D. The cross section is taken through a disruption mechanism.

FIG. 3D through FIG. 3E illustrates a transport component suitable for use with the storage component illustrated in FIG. 3A through FIG. 3C. FIG. 3D is a perspective view of a portion of the transport component. A plurality of piercing mechanisms 56 extend from a side of the transport component. The piercing mechanisms 56 serve as disruption mechanisms that can disrupt the sealing integrity of the sealing medium. FIG. 3E is a cross section of a cartridge employing the storage component of FIG. 3A and the transport component of FIG. 3D. The cross section is taken through piercing mechanism 56.

The piercing mechanisms 56 are positioned on the transport component so as to be aligned with the pockets in the storage component. Upon coupling of the storage component 12 and the transport component 13, the piercing mechanisms 56 pierce the portion of the sealing medium 50 that seals the reservoirs. Piercing of the sealing medium 50 allows the solution in a reservoir to flow into contact with a piercing mechanism 56. A lumen 57 extends through one or more of the piercing mechanisms 16 and into the transport component 13. Accordingly, the lumen 57 can transport a solution from a reservoir into the transport component 13.

As evident in FIG. 3E, the piercing mechanisms 56 are positioned on the transport component 13 so as to be aligned with the openings 53 in the base 48 of the storage component 12. The base 48 can be constructed of a material that can not be pierced by piercing mechanism 56. Accordingly, the piercing mechanisms pierce the portion of the sealing medium extending across the openings. As a result, the base 48 limits the location of disruptions created by a piercing mechanism 56 to a localized region of the sealing medium 50.

Figure 4A:
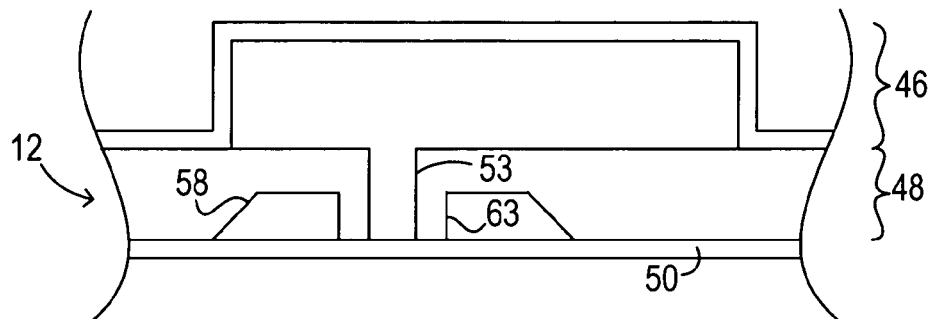
FIG. 4A through FIG. 4D illustrate a cartridge employing a different embodiment of a disruption mechanism.
Figure 4B:
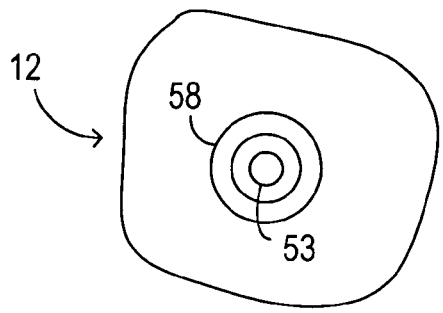
Figure 4C:
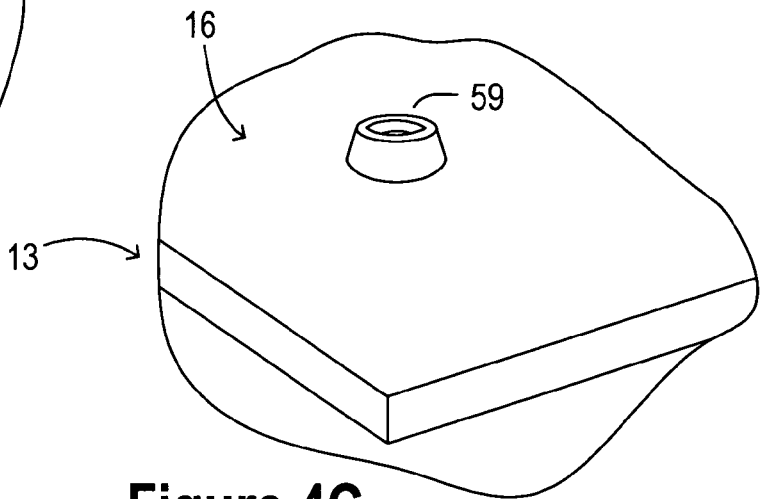
Figure 4D:
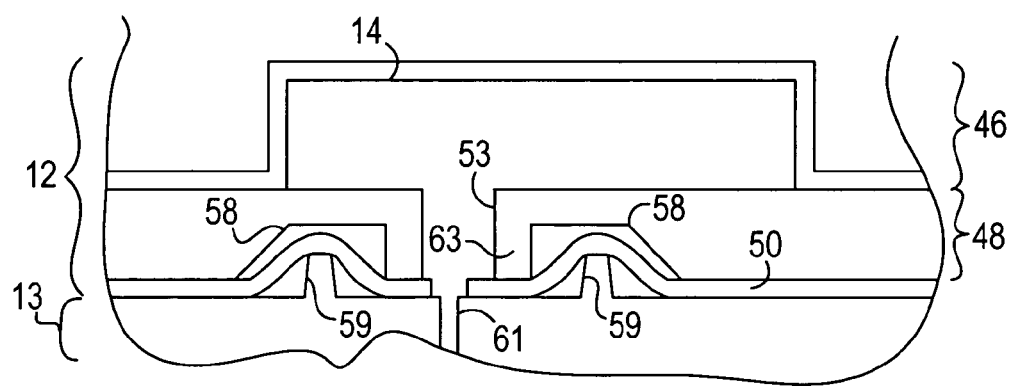

FIG. 4A through FIG. 4D illustrate a cartridge employing a different embodiment of a disruption mechanism 16. FIG. 4A is a cross section of a storage component 12 taken along the line labeled B in FIG. 3A. The storage component 12 includes a cover 46, a base 48 and a sealing medium 50. FIG. 4B is a bottomview of the storage component 12 shown in FIG. 4A without the sealing medium 50 in place. FIG. 4C is a perspective view of a portion of the transport component having the disruption mechanism. FIG. 4D is a cross section of a cartridge employing the disruption mechanism 16 illustrated on the transport component 13 of FIG. 4C.

An opening 53 extends through the base 48 of the storage component 12 so as to provide fluid pathway from a reservoir 14. The base 48 includes a recess 58 extending into the bottom of the base 48 and surrounding the opening 53. Before coupling the transport component with the storage component, the sealing medium 50 extends across the recess 58 and the opening 53 and accordingly seals the opening 53 as evident in FIG. 4A.

A ridge 59 extending from a side of the transport component shown in FIG. 4C defines a cup on the side of the transport component 13. The cup serves as a disrupting mechanism 16. Upon coupling of the storage component 12 and the transport component 13, the cup pushes a portion of the sealing medium 50 into the recess 58 as shown in FIG. 4D. The pushing motion stretches the sealing medium 50. The sealing medium 50 can include one or more channels that open upon stretching but that are closed without stretching. The one or more channels are positioned over the opening 53 and/or over the recess 58. As a result, the solution in a reservoir 14 can flow from the reservoir 14 through the one or more channels into contact with the disruption mechanism 16. Accordingly, the one or more channels opened by a cup each serve as a disruption in the sealing integrity of the sealing medium. An opening 61 extends from the bottom of the cup into the transport component 13. As a result, the solution can flow from the reservoir 13, through the one or more disruptions in the sealing medium 50 and into the transport component 13.

Suitable sealing media for use with the cups includes, but is not limited to, thermoplastic elastomers (TPEs).

Although the recess 58 is illustrated as surrounding the opening 53 and spaced apart from the opening such that a lip 63 is formed around the opening 53, the recess 58 need not be spaced apart from the opening. For instance, the recess 58 can transition directly into the opening 53 such that the lip 63 is not present. When the lip 63 is not present, the disruption mechanism can be structured as a cup, as a blunted piercing mechanism or as a combination of the two.

Although the recess is disclosed as surrounding the opening, the recess 58 can be positioned adjacent to the opening 53 without surrounding the opening 53 and the associated disruption mechanism 16 can include ridges configured to be received by the recess 58. Although FIG. 4C illustrates a transport component 13 having a single disruption mechanism 16 that includes a cup, more than one or all of the disruption mechanisms on the transport component can include a cup. Further, a transport component can include a combination of piercing mechanisms and cups that serve as disruption mechanisms.

When pockets serve as the reservoirs in the storage component, the pockets can be deformable when an external pressure is applied. During operation of the cartridge 10, an operator can apply pressure to a pocket to drive a solution from within the reservoir and into the transport component 13. Accordingly, pressure applied to the pockets can be employed to transport solution from a reservoir into the transport component. A material for the cover 46 of the storage component 12 such as PVC or polyurethane allows a pocket 52 to be deformed by application of a pressure to the pocket 52.

Although each of the storage components illustrated above having a single sealing medium extending across each of the openings 53, the storage component can include more than one sealing medium and each of the sealing media can extend across one or more of the openings.

Although not illustrated, the sealing media 50 disclosed above can include a secondary sealing layer positioned over the primary layer. The secondary sealing layer can be applied to the storage component after solutions are loaded into the reservoir(s) 14 on the storage component 12 and can be selected to prevent leakage of the solutions through the sealing medium 50 during transport and/or storage of the storage component. The secondary sealing layer can be removed before the cartridge is assembled or can be left in place. A suitable material for the secondary sealing layer includes, but is not limited to, Mylar. The secondary sealing layer can be attached to the storage component with an adhesive or using surface tension.

Figure 5A:
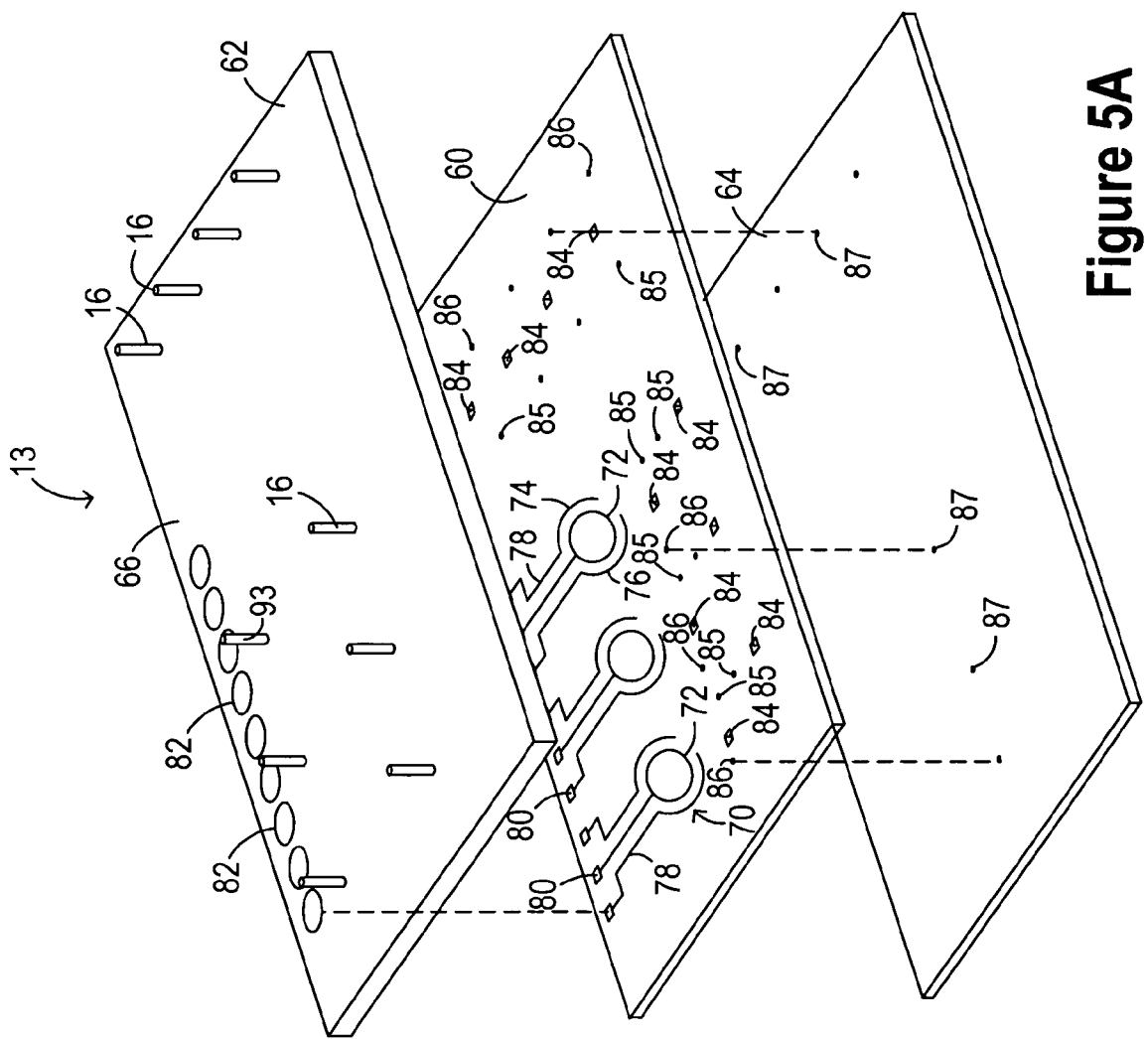
FIG. 5A through FIG. 5F illustrate a suitable construction for a transport component configured to operate as disclosed with respect to FIG. 2.
Figure 5B:
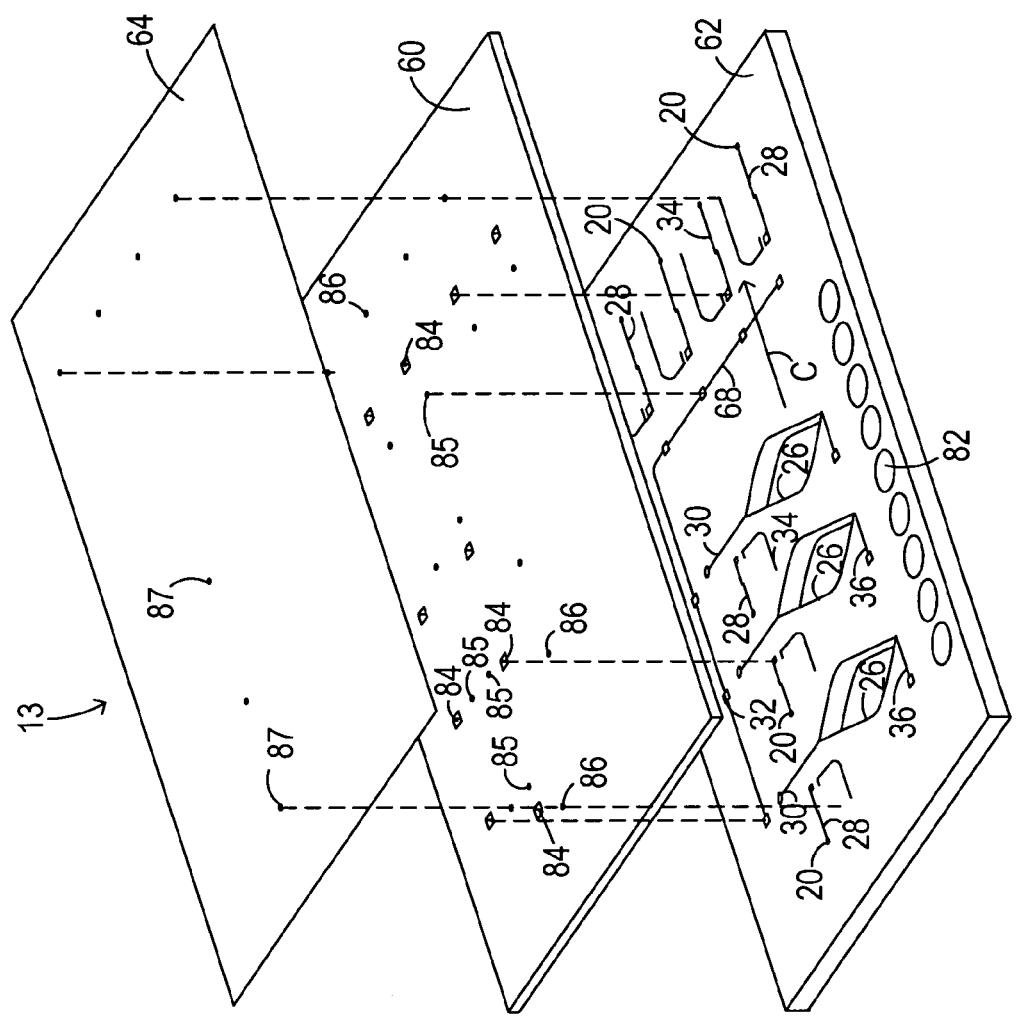
Figure 5C:
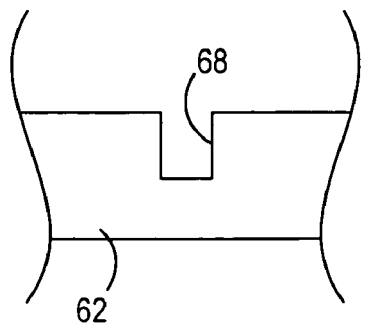

FIG. 5A through FIG. 5C illustrate a suitable construction for a transport component 13 configured to operate as disclosed with respect to FIG. 2. FIG. 5A is a perspective view of the parts of a transport component 13 before assembly of the transport component 13. FIG. 5B is a different perspective view of the parts of a transport component 13 before assembly of the transport component 13. The view of FIG. 5B is inverted relative to the view of FIG. 5A. The transport component 13 includes a base 60 positioned between a cover 62 and a flexible layer 64. FIG. 5C is a cross section of the cover 62 shown in FIG. 5B taken along the line labeled C.

The cover 62 includes a plurality of disruption mechanisms 16 extending from a common platform 66. Recesses 68 extend into the bottom of the cover 62 as is evident in FIG. 5B and FIG. 5C. As will become evident below, these recesses 68 define the top and sides of the channels and the sensor chambers 26 in the transport member. For instance, the sides of the recesses 68 serve as the sides of the channels and the sides of the sensor chamber 26. The sensor chambers 26 are positioned such that each sensor on the base 60 is positioned in a sensor chamber 26 upon assembly of the transport component 13. The cover 62 also include a plurality of openings 20 that each serve as the opening 20 to a lumen that leads to a disruption mechanism 16.

The base 60 includes a plurality of sensors 70 for detecting the presence and/or amount of an agent in a solution. The sensors 70 are positioned on the base 60 such that each sensor is positioned in a sensor chamber upon assembly of the transport component. The illustrated sensors include a working electrode 72, a reference electrode 74 and a counter electrode 76. In some instances, each of the electrodes is formed from a single layer of an electrically conductive material. Suitable electrically conductive materials, include, but are not limited to, gold. Electrical leads 78 provide electrical communication between each of the electrodes and an electrical contact 80. Other sensor constructions are disclosed in U.S. patent application Ser. No. 09/848,727, filed on May 5, 2001, entitled "Biological Identification System with Integrated Sensor Chip and incorporated herein in its entirety.

Upon assembly of the transport component the electrical contacts 80 can be accessed through openings 82 that extend through the cover 62. Although not illustrated, the storage component can include a plurality of openings that align with the openings 82 so the electrical contacts 80 can be accessed through both the openings 82 in the transport component and the openings in the storage component. Alternately, the storage component can be configured such that the openings 82 in the transport component remain exposed after assembly of the cartridge. In these instances, the contacts can be accessed through the openings 82 in the transport component.

A plurality of first valve channels 84 and second valve channels 85 extend through the base 60. As will become evident below, each first valve channel 84 is associated with a second valve channel 85 in that the first valve channel 84 and associated second valve channel 85 are part of the same valve. Upon assembly of the transport component: a portion of the first valve channels 84 are aligned with an inlet channel 28 such that a solution flowing through an inlet channel can flow into the first valve channel and the associated second valve channels are aligned with a common channel such that a solution in the second valve channel can flow into the common channel; a portion of the first valve channels 84 are aligned with an inlet channel 28 such that a solution flowing through an inlet channel can flow into the first valve channel and the associated second valve channels are aligned with an independent channel such that a solution in the second valve channel can flow into the independent channel; and a portion of the first valve channels 84 are aligned with an common channel 28 such that a solution flowing through the common channel can flow into the first valve channel and the associated second valve channels are aligned with an independent channel such that a solution in the second valve channel can flow into the independent channel. As will become evident below, the first valve channels 84 can serve as valve inlets and the second valve channels 84 can serve as valve outlets.

First vent openings 86 also extend through the base 60. Upon assembly of the transport component the first vent openings 86 align with the vent channels 34 such that air in each vent channel 34 can flow through a first vent opening 86. The flexible layer 64 includes a plurality of second vent openings 87. The second vent openings 87 are positioned such that each second vent opening 87 aligns with a first vent opening 86 upon assembly of the transport component. As a result, air in each vent channel 34 can flow through a first vent opening 86 and then through a second opening. Accordingly, air in each vent channel can be vented to the atmosphere.

Figure 5D:
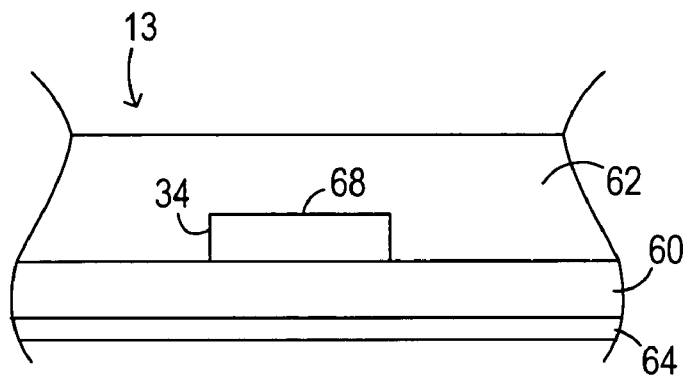

The transport component 13 can be assembled by attaching the base 60 to the cover 62 and the flexible layer 64. Upon assembly of the transport component 13, the channels are partially defined by the base 60 and the recesses 68 in the cover 62. For instance FIG. 5D is a cross section of a portion of the transport component 13 having a vent channel 34. The cover 62 defines the top and sides of the vent channel 34 while the base 60 defines the bottom of the vent channel 34.

The transport component 13 is configured such that air can flow through the vent channels 34 while restricting solution flow through the vent channel 34. In some instances, the vent channels 34 are sized to allow airflow through the vent channel 34 while preventing or reducing the flow of solution through the vent channel 34.

Figure 5E:
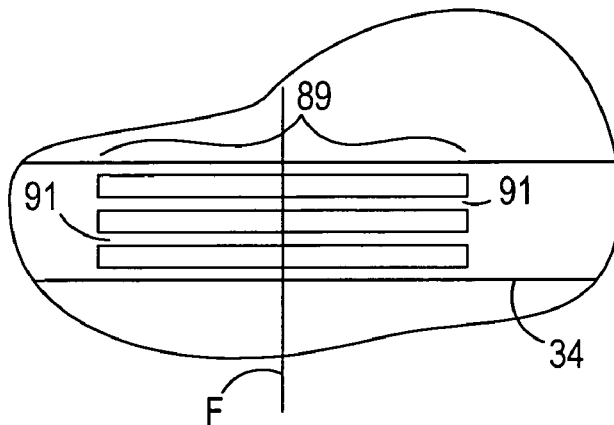
Figure 5F:
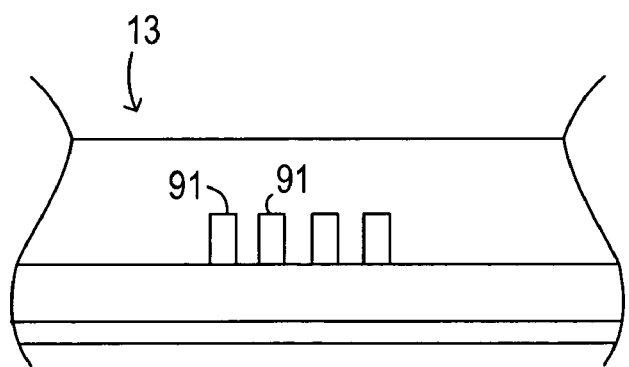

In some instances, a vent channel 34 includes one or more constriction regions 89. The constriction region 89 can include a plurality of ducts, conduits, channels or pores through an obstruction in the vent channel. The ducts, conduits, channels or pores can each be sized to permit air flow while obstructing solution flow. For instance, FIG. 5E is bottom view of the portion of a cover 62 having a vent channel 34 with a constriction region 89. FIG. 5F is a cross section of the constriction region 89 taken at the line labeled F. The constriction region 89 includes a plurality of ducts 91 that are each sized to permit airflow while restricting or obstructing solution flow. In some instances, the ducts 91 each have a cross sectional area less than 0.01 $\mu m^2$. The use of multiple ducts 91 can increase the amount of airflow above the level that can be achieved with a single duct or a single channel configured to restrict solution flow. As a result, multiple ducts 91 can increase the efficiency with which air can flow through the vent channel 34. A constriction region 89 can be positioned anywhere along the vent channel 34 and multiple constriction regions can be used along a single vent channel 34. Additionally, the constriction region 89 can extend the entire length of the vent channel 34.

Alternatively or additionally, a membrane (not shown) can be positioned on the flexible layer 64 so as to cover one or more of the second vent openings 87. The membrane can be selected to allow the passage of air through the membrane while preventing the flow of solutions through the membrane. As a result, the membrane can obstruct solution flow through a vent channel 34. The membrane can be positioned locally relative to the second vent openings. For instance, the membrane can be positioned so as to cover one or more of the second vent openings. Alternately, the membrane can be a layer of material positioned on the flexible layer 64 and covering a plurality of the second vent openings 87. A suitable material for the membrane includes, but is not limited to PTFE. When a membrane is employed, the vent channel can also be configured to restrict solution flow but need not be. For instance, one or more constriction regions 89 can optionally be employed with the membrane.

The cover 62 illustrated in FIG. 5A includes a plurality of waste outlet structures 93 extending from the common platform 66. These outlet structures align with the waste channels 36 upon assembly of the transport component and provide an outlet for waste solution from a sensor chamber 26. The outlet structures can be a piercing mechanism that pierce an empty reservoir 14 on the storage component upon assembly of the cartridge. In these instances, the waste solution flows into the reservoir 14 during operation of the cartridge. Alternately, the outlet structures can be accessible above the cartridge. For instance, the outlet structures can extend through or around the storage component. In these instances, the outlet structures can be connected to a tube or other device that carries the waste solution away from the cartridge. The outlet structures need not be present on the storage device. In these instances, the transport component can include an internal reservoir into which the waste solutions can flow. For instance, the base 60 and the cover 62 can define a waste reservoir into which the waste channels 36 flow.

The cover 62 and the base 60 can be formed by techniques including, but not limited to, injection molding. A suitable material for the cover 62 and base 60 include, but are not limited to polycarbonate. A suitable flexible layer 64 includes, but is not limited to, an elastic membrane. Suitable techniques for bonding the cover 62 and the base 60 include, but are not limited to, laser welding or using an adhesive. A variety of technologies can be employed to bonding the base 60 and the flexible layer 64. For instance, laser welding can be used to bond the base 60 and the flexible layer 64. As will become evident below, there are regions of the transport component where the flexible layer 64 is not bonded to the transport component. These regions can be formed through the use of a shadow mask in conjunction with laser welding. The electrodes, electrical contacts and electrical leads can be formed on the base using integrated circuit fabrication technologies.

Figure 6A:
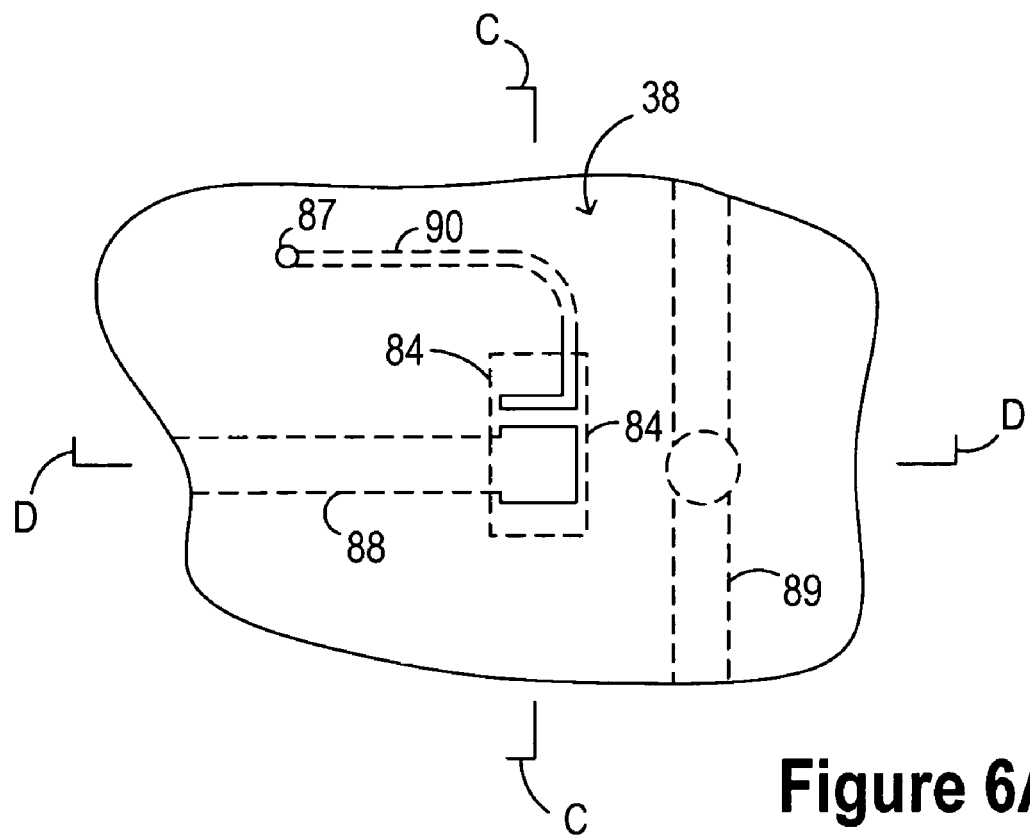
FIG. 6A through FIG. 6E illustrates a valve formed upon assembly of the transport component.
Figure 6B:
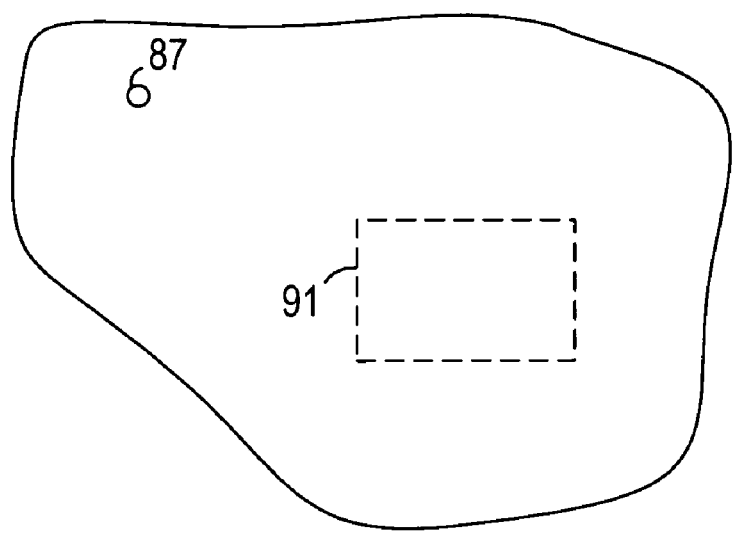
Figure 6C:
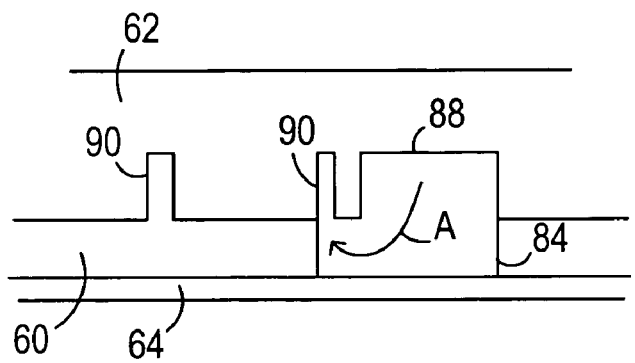
Figure 6D:
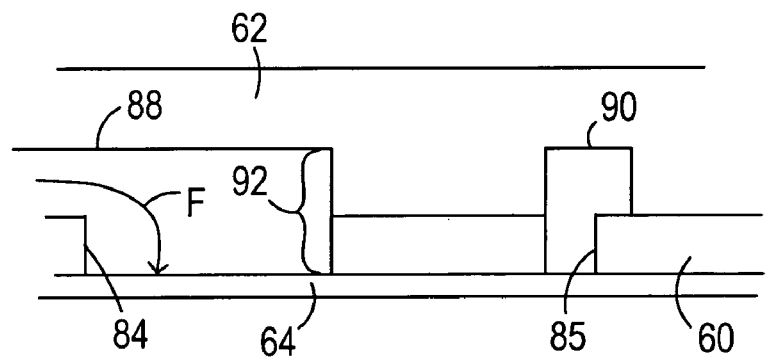

The cover 62, the base 60 and the flexible layer 64 form the valves in the transport mechanism. FIG. 6A through FIG. 6E illustrate one of the valves formed upon assembly of the transport component shown in FIG. 5A and FIG. 5B. FIG. 6A is a topview of the portion of the transport component that includes the valve. The dashed lines illustrate items that are positioned in the interior of the transport component. FIG. 6B is a bottom view of the portion of the transport component shown in FIG. 6A. The dashed lines in FIG. 6B illustrate the location of a valve region 91 where the flexible layer 64 is not attached to the base 60. FIG. 6C is a cross section of the cartridge shown in FIG. 6A taken along a line extending between the brackets labeled C. FIG. 6D is a cross section of the cartridge shown in FIG. 6A taken along a line extending between the brackets labeled D.

A first valve channel 84 in the base 60 is aligned with an input channel 88 in the cover 62 such that a solution in the input channel can flow into the first valve channel. Accordingly, the first valve channel 84 defines a portion of the input channel. A second valve channel 85 in the base 60 is aligned with an output channel 89 in the cover 62 such that a solution in the second valve channel can flow into the output channel. Accordingly, the second valve channel 84 defines a portion of the output channel. The base 60 and the cover 62 act together to form an obstruction 92 between the input channel 88 and the output channel 89. Additionally, the cover provides a second obstruction between the input channel and the vent channel. The flexible material is positioned over the obstruction 92, the first valve channel and the second valve channel. As a result, the flexible material is positioned over a portion of the input channel and a portion of the output channel. Further, the flexible material is positioned over a portion of the vent channel.

Figure 6E:
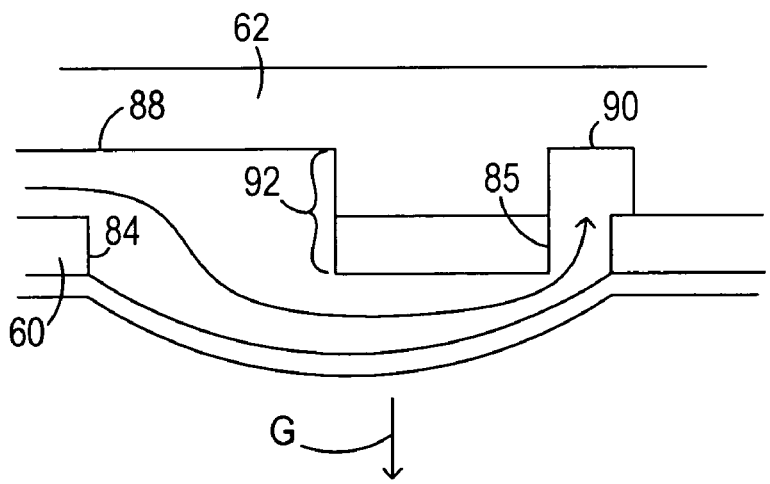

FIG. 6D through FIG. 6E illustrate operation of the valve. The desired direction of the solution flow through the valve is illustrated by the arrow labeled F in FIG. 6D. The flexible layer 64 is positioned close enough to the obstruction 92 that the solution does not flow around the obstruction 92 before a threshold pressure is applied to the solution upstream of the valve. As a result, FIG. 6D illustrates the valve before the solution flows through the valve. As the solution flows toward the valve, air in the input channel 88 can exit the input channel 88 through the vent channel 90 as illustrated by the arrow labeled A in FIG. 6C. The vent channel 90 is constructed such that the air can flow through the vent channel 90. In some instances, solution can also flow through all or a portion of the vent channel length. In instances where solution flows into the vent channel, one or more constriction regions can option be positioned along the vent channel as discussed in the context of FIG. 5. As a result, the vent channel 90 allows air and/or other gasses to be vented from the input channel 88. A portion of the vent channel 90 is shown as being parallel to the input channel 88 in the valve region. The parallel nature of the vent channel 90 allows the air to continue draining while the valve region fills with solution.

During operation of the valve, the displacement between the flexible layer 64 and the obstruction 92 changes. For instance, as the valve opens from a closed position or as the valve opens further, the flexible layer 64 moves away from the obstruction 92 as shown in FIG. 6E. The movement of the flexible layer 64 away from the obstruction 92 increases the volume of a fluid path around the obstruction 92. Once the upstream pressure on the solution passes a threshold pressure, the solution begins to flow through the fluid path around the obstruction 92 as illustrated by the arrow labeled F in FIG. 6E. Accordingly, the movement of the flexible layer away from the obstruction allows the solution to flow from the input channel 88 into the output channel 89.

Figure 7A:
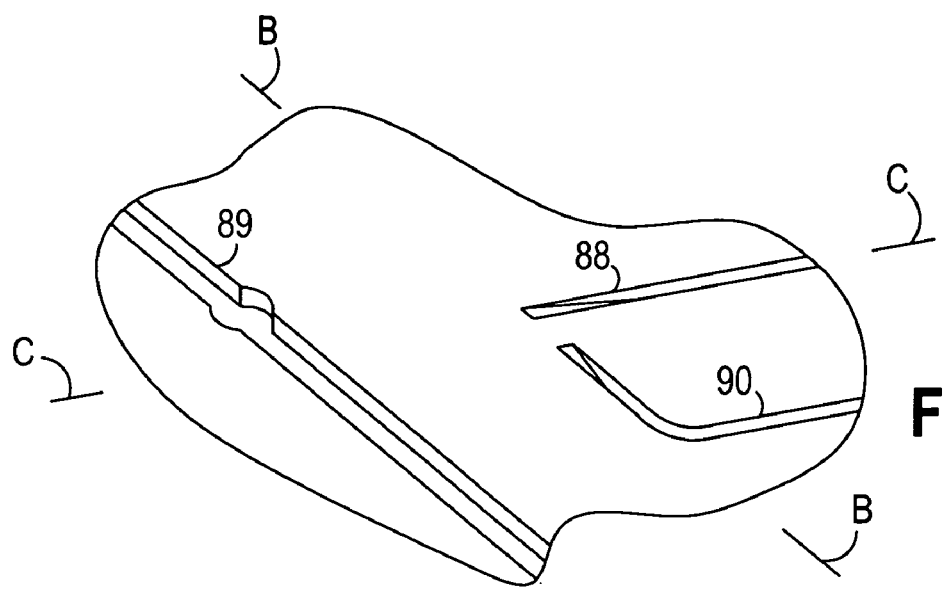
FIG. 7A through FIG. 7D through illustrate another embodiment of a valve suitable for use with the cartridge.
Figure 7B:
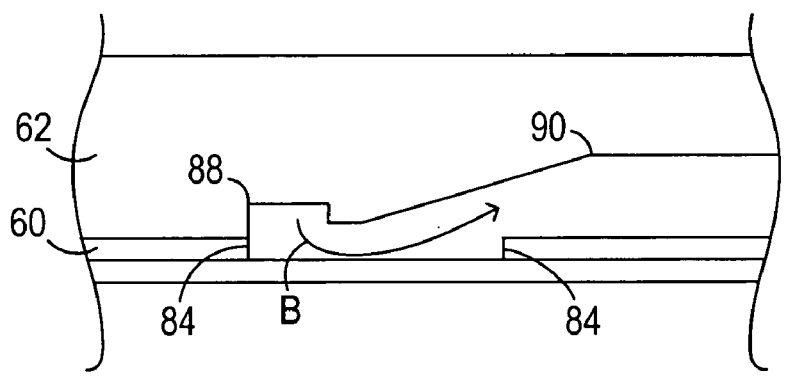
Figure 7C:
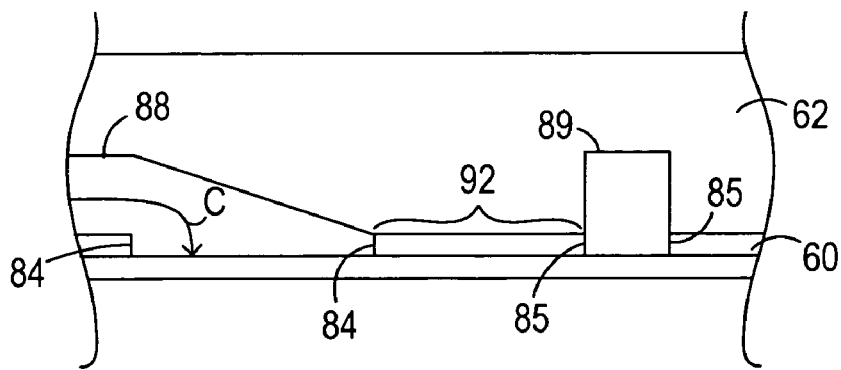

FIG. 7A through FIG. 7C through illustrate another embodiment of a valve suitable for use with the cartridge. FIG. 7A is a perspective view of the portion of the cover that includes the valve. FIG. 7B illustrates a cross section of a transport component that includes the cover 62 shown in FIG. 7A taken along a line extending between the brackets labeled B. FIG. 7C illustrates a cross section of a transport component that includes the cover 62 shown in FIG. 7A taken along a line extending between the brackets labeled C.

A first valve channel 84 in the base 60 is aligned with an input channel 88 in the cover 62 such that a solution in the input channel can flow into the first valve channel. Accordingly, the first valve channel 84 defines a portion of the input channel. A second valve channel 85 in the base 60 is aligned with an output channel 89 in the cover 62 such that a solution in the second valve channel can flow into the output channel. Accordingly, the second valve channel 84 defines a portion of the output channel. The base 60 and the cover 62 act together to form an obstruction 92 between the input channel 88 and the output channel 89. Additionally, the cover provides a second obstruction between the input channel and the vent channel. The flexible material is positioned over the obstruction 92, the first valve channel and the second valve channel. As a result, the flexible material is positioned over a portion of the input channel and a portion of the output channel. Further, the flexible material is positioned over a portion of the vent channel.

Figure 7D:
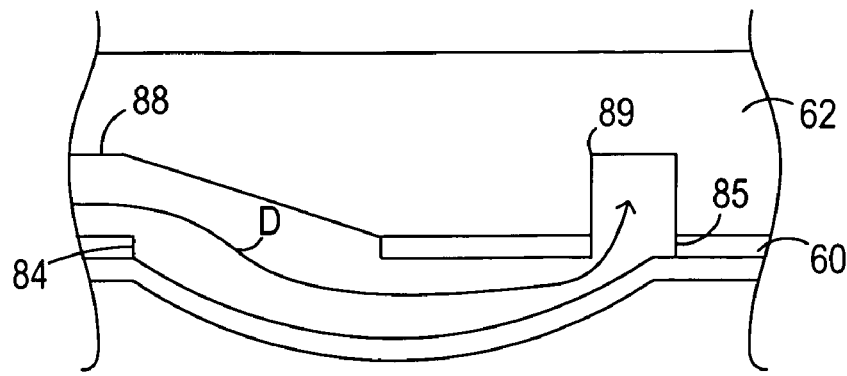

FIG. 7B and FIG. 7D illustrate operation of the valve. The desired direction of the solution flow through the valve is illustrated by the arrow labeled C in FIG. 7C. The flexible layer 64 is positioned close enough to the obstruction 92 that the solution does not flow around the obstruction 92 before a threshold pressure is applied to the solution upstream of the valve. As a result, FIG. 7C illustrates the valve before the solution flows through the valve. As the solution flows toward the valve, air in the input channel 88 can exit the input channel 88 through the vent channel 90 as illustrated by the arrow labeled B in FIG. 7B. In some instances, solution can also flow into the vent channel. In instances where solution flows into the vent channel, one or more constriction regions can option be positioned along the vent channel as discussed in the context of FIG. 5. Accordingly, the vent channel 90 can be constructed such that the air can flow through the vent channel 90 but the solution is prevented from flowing through the vent channel 90. As a result, the vent channel 90 allows the air to drain from the input channel 88.

When the valve opens, the flexible layer 64 moves away from the obstruction 92 as shown in FIG. 7D. The movement of the flexible layer 64 away from the obstruction 92 creates a fluid path around the obstruction 92. Once the upstream pressure on the solution passes a threshold pressure, the solution begins to flow through the fluid path around the obstruction 92 as illustrated by the arrow labeled D in FIG. 7D. Accordingly, the movement of the flexible layer away from the obstruction allows the solution to flow from the input channel 88 into the output channel 89.

One or more of the channels that intersect at the valve can have a volume that decreases as the channel approaches the valve. The portion of a channel opposite the flexible material can slope toward the flexible material as the channel approaches the valve as is evident in FIG. 7C. For instance, the portion of the input channel 88 that ends at the valve can have a height that tapers in a direction approaching the valve. The height of a channel is the height of the channel at a point along the channel being measured in a direction perpendicular to the flexible material and extending from the flexible material across the channel to the point of the opposing side located furthest from the flexible material. The slope reduces the nearly perpendicular corner that can be formed between the side and bottom of an input channel 88 at location where the channel ends at the valve. A sharp corner can serve as a pocket where air can be caught. The slope can help to smooth the corner and can accordingly reduce formation of air bubbles in these pockets.

FIG. 7A through FIG. 7D also show the height of the vent channel 90 tapering toward the valve. This taper can prevent the formation of air pockets in the vent channel 90. Although FIG. 7A through FIG. 7D show tapers in the height of the input channel 88 and the vent channel 90, the valve can be constructed such that neither the input channel 88 nor the vent channel 90 includes a taper; such that the input channel 88 includes the taper and the vent channel 90 excludes the taper; or such that the vent channel 90 includes the taper and the input channel 88 excludes the taper.

The portion of the vent channel 90 closest to the input channel 88 at the valve can be parallel to the adjacent portion input channel 88 as is evident in FIG. 7A. The length of the parallel portion can optionally be about the same as the width of the adjacent portion of the input channel 88. This construction can reduce the formation of air bubbles in the valve.

The arrangement of the input channel 88, the output channel 89 and the vent channel 90 relative to one another can be changed from the arrangement illustrated in FIG. 6A through FIG. 7D. For instance, the portion of the output channel and the input channel 88 at the intersection of the channel can both be parallel to the output channel as illustrated by the valve labeled V in FIG. 2. Although FIG. 2 illustrates the valve positioned part way along the inlet channel, the valve can be constructed so the valve is positioned at an intersection of the inlet channel, vent channel and common channel. The flexibility in channel arrangement can increase the number of features that can be placed on a single cartridge.

In some instances, the second valve channel has a substantially round shape as evident in FIG. 6A. The round shape may have a diameter that is larger than the width of the output channel. In these instances, the output channel can optionally have a bulge as is evident in FIG. 6A and FIG. 7A. The bulge can be configured to make the walls of the output channel substantially flush with the walls of the second valve channel. The flush nature can reduce the formation of air pockets that can result from formation of a step between the walls of the output channel and the walls of the second valve channel.

The valves disclosed in FIG. 6A through FIG. 7D can be the first valves 38 or the third valves 42 described in the context of FIG. 2. When the valve serves as a first valve 38, an inlet channel 28 can be the input channel 88, a common channel 32 can be the output channel 89, and a vent channel 34 can be the vent channel 90. Alternately, the valve can be positioned part way along the inlet channel. For instance, a portion of an inlet channel 28 can be the input channel 88, another portion of the inlet channel 28 can be the output channel 89, and a vent channel 34 can be the vent channel 90.

When the valve serves as a third valve 42, an inlet channel 28 can be the input channel 88, an independent channel 30 can be the output channel 89, and a vent channel 34 can be the vent channel 90. Alternately, the valve can be positioned part way along the inlet channel. For instance, a portion of an inlet channel 28 can be the input channel 88, another portion of the inlet channel can be the output channel 89, and a vent channel 34 can be the vent channel 90.

The valves disclosed in FIG. 6A through FIG. 7D can be adapted to serve as the second valve 40 described in the context of FIG. 2 by removing the vent channel 34 from the valve. When the valve serves as a second valve 40, a common channel 28 can be the input channel 88 and an independent channel 30 can be the output channel 89. Alternately, the valve can be positioned part way along the independent channel 30. For instance, a portion of an independent channel 30 can be the input channel 88, another portion of the independent channel 30 can be the output channel 89.

Although the transport component illustrated in FIG. 5A and FIG. 5B includes valves constructed according to FIG. 6A through FIG. 6E, one of the valves, more than one of the valves or all of the valves can be constructed according to FIG. 7A through FIG. 7E.

The above valves can be opened by increasing the upstream pressure on the solution enough to deform the flexible layer 64 and/or by employing an external mechanism to move the flexible layer 64 away from the obstruction 92. The upstream pressure can be increased by compressing the reservoir 14 that contains a solution in fluid communication with the inlet channel. An example of a suitable external mechanism is a vacuum. The vacuum can be employed to pull the flexible layer 64 away from the obstruction 92.

Although the flexible layer 64 is illustrated as being in contact with the obstruction 92, the transport component can be constructed such that the flexible layer 64 is spaced apart from the obstruction 92 when the positive pressure is not applied to the upstream solution. A gap between the flexible layer 64 and the obstruction 92 can be sufficiently small that the surface tension of the solution prevents the solution from flowing past the obstruction 92 until a threshold pressure is reached. In these instances, the movement of the flexible layer 64 away from the obstruction 92 serves to increase the volume of the path around the obstruction 92.

The threshold pressure that is required to generate solution flow through the valve can be controlled. A stiffer and/or thicker flexible layer 64 can increase the threshold pressure. Moving the flexible layer 64 closer to the obstruction 92 when the positive pressure is not applied to the upstream solution can increase the threshold pressure. Decreasing the size of one or more of the valve channels 84 can narrow the fluid path around the obstruction 92 can also increase the threshold pressure. Further, in creasing the size of one or more of the valve channels 84 can increase the volume of the path around the obstruction 92 can also reduce the threshold pressure.

The relative size of the inlet valve channel 84 and the outlet valve channel 84 can also play a role in valve performance. For instance, a ratio of the cross-sectional area of the outlet valve channel 84 to cross-sectional area of the inlet valve channel 84 can affect valve performance. Back flow through the valve can be reduced when this ratio is less than one. Additionally, reducing the ratio serves to reduce the backflow. In some instances, the inlet channel and/or the outlet channel has more than one flow path. For instance, the outlet flow channel can include a plurality of holes through the base. In these instances, the cross sectional area of the outlet channel is the sum of the total cross sectional area of each of the flow paths.

Although the valve is disclosed in the context of a valve positioned between an inlet channel and a common channel 32, the illustrated valve construction can be applied to the other valves in the transport component.

Although the above illustrations show the vent channel 34 as being connected to the valve, vent channels 34 can be positioned at a variety of other locations. For instance, a vent channel 34 can be positioned in the inlet channel before the valve.

Although the transport components of FIG. 5A and FIG. 5B illustrate a single flexible material forming each of the valves, the transport component can include more than one flexible material and each of the flexible material can be included in one valve or in more than one valve.

Figure 8A:
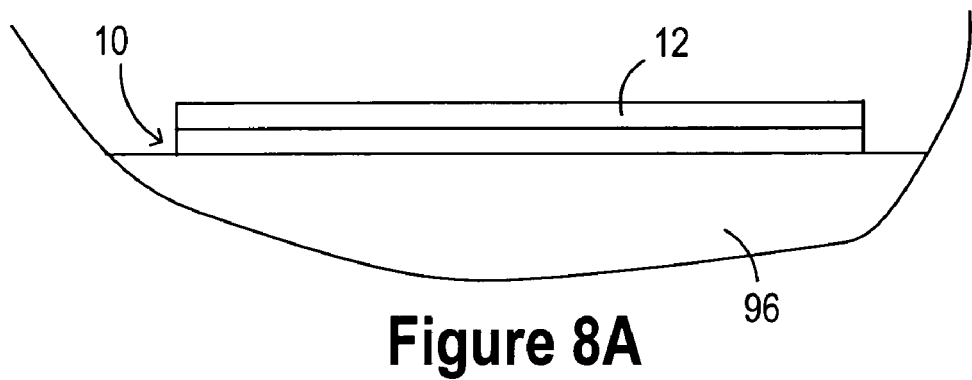
FIG. 8A and FIG. 8B illustrate operation of the cartridge.
Figure 8B:
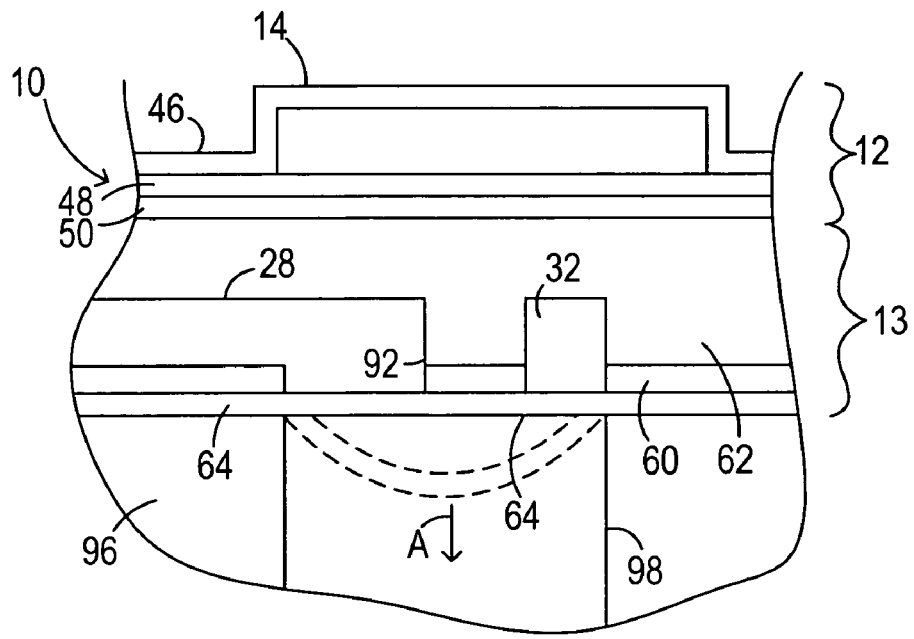

FIG. 8A and FIG. 8B illustrate operation of the cartridge constructed as disclosed above with an external mechanism employed to move a flexible layer 64 away from a obstruction 92 in a valve. FIG. 8A is a sideview of a system including the cartridge positioned on a manifold 96. FIG. 8B is a cross section of the system shown in FIG. 8A. The manifold 96 includes a plurality of vacuum ports 98. The ports are aligned with the valves on the cartridge. The manifold 96 is configured such that a vacuum can be independently pulled on one or more of the ports. The amount of vacuum pulled at a vacuum port 98 can be sufficient to completely or partially open the valve aligned with that port as illustrated by the dashed line and the arrow labeled A in FIG. 8B. As a result, the manifold 96 can be employed to selectively open the valves on the cartridge. In some instances, the manifold is also configured to generate a positive pressure on one or more vacuum ports. The positive pressure can keep one or more valves closed during operation of the cartridge. For instance, the manifold can be operated so as to keep a second valve 40 (shown in FIG. 2) closed while a solution is flowed through the associated third valve 42 and into the associated independent channel. Keeping the second valve closed can reduce backflow of the solution into the common channel. In some instances, the desired fluid flow through the cartridge is achieved through the combined use of the manifold 96 and the application of external pressure to the reservoirs 14 of the storage component.

Although a manifold 96 is disclosed in FIG. 8A and FIG. 8B, a cartridge constructed as disclosed above may operate without the use of an external mechanism for opening and closing of the valves. As a result, the manifold 96 is optional.

Although the cartridge is shown a having a single disruption mechanism associated with each reservoir, the cartridge can include more than one disruption mechanism associated with each reservoir and/or the base of the storage component can include more than one opening associated with each reservoir.

Although the transport component is disclosed above as including an electrochemical sensor other sensor types can be employed in conjunction with the cartridge. Further, the above cartridges can be adapted to include one sensor, two sensors or more than three sensors.

The invention claimed is:

1. A cartridge, comprising:
a storage component including reservoirs that each contains a solution, the storage component including a cover and a base,
the cover having pockets extending from a side of a common platform, each pocket defining a portion of one of the reservoirs,
the base having openings extending through the base such that the openings are each aligned with a different one of the pockets;
a transport component separate from the storage component and configured to be coupled with the storage component,
the transport component being configured to transport the solutions from the reservoirs to a sensor held by the transport component, the sensor being configured to detect a presence and/or amount of an agent in a liquid sample,
the transport component includes disruption mechanisms configured to be received in the openings upon coupling of the storage component and the transport component.

2. The cartridge of claim 1, wherein the disruption mechanisms are configured to disrupt the sealing integrity of a material on the storage component upon coupling of the transport component and the storage component, the sealing integrity being disrupted so as to provide an outlet through which a solution in a reservoir can flow out of the storage component through one of the openings.

3. The cartridge of claim 1, wherein the transport mechanism includes lumens that are each positioned so as to transport the solution flowing from one of the reservoirs into the transport component.

4. The cartridge of claim 2, wherein one or more of the disruption mechanisms includes a piercing mechanism configured to pierce the material.

5. The cartridge of claim 4, wherein a lumen extends through the piercing mechanism.

6. The cartridge of claim 1, wherein one or more of the disruption mechanisms include a cup.

7. The cartridge of claim 6, wherein a lumen extends from the bottom of the cup into the transport component.

8. The cartridge of claim 2, wherein one or more of the disruption mechanisms is configured to stretch the material upon coupling of the storage component and the transport component.

9. The cartridge of claim 1, wherein the openings extend through the base such that the solution in each one of the reservoirs can flow into the opening aligned with that reservoir.

10. The cartridge of claim 9, wherein a single and continuous material serves as the cover.

11. The cartridge of claim 9, wherein the storage component includes a single and continuous sealing medium poisoned on the base so as to seal the openings.

12. A cartridge, comprising:
a storage component including reservoirs that each contains a solution, the storage component including pockets extending from a side of a common platform, each pocket defining a portion of one of the reservoirs; and
a transport component separate from the storage component and configured to be coupled with the storage component,
the transport component being configured to transport the solutions from the reservoirs to a sensor held by the transport component, the sensor being configured to detect a presence and/or amount of an agent in a liquid sample, and
the transport component including a valve configured to control the flow of a solution around an obstruction positioned between an input channel in the transport component and an output channel in the transport component, the valve including a flexible material positioned over the obstruction and a portion of the input channel and a portion of the output channel.

13. The cartridge of claim 12, wherein an opposite side of the input channel from the flexible material slopes toward the flexible material.

14. The cartridge of the claim 12, wherein a height of the input channel decreases moving toward the valve, the height of the channel at a point along the channel being measured in a direction perpendicular to the flexible material and extending from the flexible material across the channel to the point of the opposing side located furthest from the flexible material.

15. The cartridge of claim 12, wherein the transport component includes a vent channel extending away from the valve, the vent channel being configured to vent gasses from the channel during operation of the valve.

16. The cartridge of claim 15, wherein an opposite side of the vent channel from the flexible material slopes toward the flexible material.

17. The cartridge of the claim 15, wherein a height of the vent channel decreases moving toward the valve when the valve is closed, the height of the channel at a point along the channel being measured in a direction perpendicular to the flexible material and extending from the flexible material across the channel to the point of the opposing side located furthest from the flexible material.

18. The cartridge of claim 12, wherein the transport component includes a cover positioned on a base, the cover and the base defining the input channel and an output channel, the base including:
   a first valve channel extending through the base and positioned over a portion of the input channel; and
   a second valve channel extending through the base and positioned over a portion of the output channel, the flexible material being positioned over the first valve channel opening and over the second valve channel.

19. The cartridge of claim 12, wherein the cover and the base define a vent channel, the first valve channel being positioned over a portion of the vent channel.

20. A transport component for use with a cartridge, comprising:
   a transport component configured to be coupled with a storage component that is separate from the transport component, the storage component having reservoirs that each hold a solution;
   the transport component being configured to transport the solutions from the reservoirs to a sensor held by the transport component, the transport component including a valve configured to control the flow of a solution from an input channel in the transport component to an output channel in the transport component, the valve includes a flexible material defining a portion of the input channel; and
   the sensor being configured to detect the a presence and/or amount of an agent in a liquid sample.

21. The component of claim 20, wherein the transport component includes disruption mechanisms configured to disrupt the sealing integrity of a material on the storage component upon coupling of the transport component and the storage component, the sealing integrity being disrupted so as to provide an outlet through which a solution in a reservoir can flow out of the storage component.

22. The component of claim 21, wherein the transport mechanism includes one or more lumens positioned so as to transport the solution flowing from the reservoir into the transport component.

23. The component of claim 21, wherein one or more of the disruption mechanisms includes a piercing mechanism configured to pierce the material.

24. The component of claim 23, wherein a lumen extends through the piercing mechanism.

25. The component of claim 21, wherein one or more of the disruption mechanisms include a cup.

26. The component of claim 25, wherein a lumen extends from the bottom of the cup into the transport component.

27. The component of claim 20, wherein the flexible material defines a portion of the outlet channel.

28. The component of claim 20, wherein an opposite side of the input channel from the flexible material slopes toward the flexible material.

29. The component of claim 20, wherein a height of the input channel decreases moving toward the valve, the height of the channel at a point along the channel being measured in a direction perpendicular to the flexible material and extending from the flexible material across the channel to the point of the opposing side located furthest from the flexible material.

30. The component of claim 20, wherein the transport component includes a vent channel extending away from the valve, the vent channel being configured to vent gasses from the channel during operation of the valve.

31. The component of claim 30, wherein the flexible material is positioned over a portion of the vent channel and a side of the vent channel opposite from the flexible material slopes toward the flexible material.

32. The component of claim 30, wherein a height of the vent channel decreases moving toward the valve when the valve is closed, the height of the channel at a point along the channel being measured in a direction perpendicular to the flexible material and extending from the flexible material across the channel to the point of the opposing side located furthest from the flexible material.

33. The component of claim 28, wherein the transport component includes a cover positioned on a base, the cover and the base defining the input channel and the output channel, the base including:
   a first valve channel extending through the base and positioned over a portion of the input channel; and
   a second valve channel extending through the base and positioned over a portion of the output channel, the flexible material being positioned over the first valve channel and over the second valve channel.

34. The component of claim 28, wherein the cover and the base define a vent channel, the first valve channel being positioned over a portion of the vent channel.

35. A method, comprising:
   coupling a storage component with a transport component so as to form a cartridge, the storage component including one or more reservoirs that each contain a solution, the storage component including a cover and a base,
      the cover having pockets extending from a side of a common platform, each pocket defining a portion of one of the reservoirs,
      the base having openings extending through the base such that the openings are each aligned with a different one of the pockets; and
   the transport component configured to transport the solutions from one or more of the reservoirs to a sensor held by the transport component, the sensor being configured to detect the a presence and/or amount of an agent in a liquid sample the transport component including disruption mechanisms that are received in the openings upon coupling of the storage component and the transport component.

36. The method of claim 35, wherein coupling the storage component with the transport component causes the one or more disruption mechanisms to disrupt the sealing integrity of a material on the storage component so as to generate an outlet through which a solution in a reservoir can flow out of the storage component.

37. the method of claim 35, further comprising:
opening a valve on the transport component so as to control flow of a solution through the transport component.

38. The method of claim 37, further comprising:
applying pressure to a pocket on the storage component so as to drive the solution in the reservoir into the transport component.

39. A cartridge comprising:
a storage component including reservoirs that each contains a solution, the storage component including pockets extending from a side of a common platform, each pocket defining a portion of one of the reservoirs; and
a transport component separate from the storage component and configured to be coupled with the storage component,
the transport component being configured to transport the solutions from the reservoirs to a sensor held by the transport component, the sensor being configured to detect a presence and/or amount of an agent in a liquid sample, and
the transport component including a vent channel, an input channel and an output channel meeting at a valve, the valve being configured to control flow of a solution from the input channel to the output channel while venting gasses into the vent channel.

40. The cartridge of claim 39, further comprising:
an obstruction positioned between the input channel and the output channel; and
a flexible material positioned over the obstruction such that a displacement between the obstruction and the flexible material changes during operation of the valve.

41. The cartridge of claim 39, wherein the transport component includes a flexible material positioned over a portion of the input channel and a portion of the output channel.

42. The cartridge of claim 41, wherein the flexible material is positioned over a portion of the vent channel.

43. The cartridge of claim 39, wherein the transport component further comprises:
one or more channels configured to transport the solution from the valve to the one or more sensors.

44. The cartridge of claim 39, wherein the valve includes a flexible material defining a portion of the input channel such that the portion of the input channel defined by the flexible material has a volume that changes during operation of the valve.

45. The cartridge of claim 40, wherein a portion of the input channel opposite from the flexible material slopes toward the flexible material as the channel approaches the valve.

46. The cartridge of claim 40, wherein a height of the input channel decreases moving toward the valve when the valve is closed, the height of the channel at a point along the channel being measured in a direction perpendicular to the flexible material and extending from the flexible material across the input channel to the point of the opposing side located furthest from the flexible material.

47. The cartridge of claim 40, wherein an opposite side of the vent channel from the flexible material slopes toward the flexible material.

48. The cartridge of claim 40, wherein a height of the vent channel decreases moving toward the valve when the valve is closed, the height of the channel at a point along the channel being measured in a direction perpendicular to the flexible material and extending from the flexible material across the channel to the point of the opposing side located furthest from the flexible material.

49. The cartridge of claim 39, wherein the transport component includes a cover positioned on a base, the cover and the base defining the channel and defining an output channel, the base including:
a first valve channel extending through the base and positioned over a portion of the input channel; and
a second valve channel extending through the base and positioned over a portion of the output channel, the flexible material being positioned over the first valve channel and over the second valve channel.

50. A cartridge, comprising:
a storage component including reservoirs that each contains a solution, the storage component including pockets extending from a side of a common platform, each pocket defining a portion of one of the reservoirs; and
a transport component separate from the storage component and configured to be coupled with the storage component,
the transport component being configured to transport the solutions from the reservoirs to a sensor held by the transport component, the sensor being configured to detect a presence and/or amount of an agent in a liquid sample, and
the transport component including a valve configured to control flow of a solution around an obstruction positioned between an input channel and an output channel, the valve including a flexible material positioned over the obstruction such that a displacement between the obstruction and the flexible material changes during operation of the valve, a portion of the input channel sloping toward the flexible material when moving along the input channel toward the valve.

51. The cartridge of claim 50, wherein the flexible material is positioned over a portion of the input channel and a portion of the output channel.

52. The cartridge of claim 51, wherein the flexible material is positioned over a portion of the vent channel.

53. The cartridge of claim 50, wherein the transport component further comprises:
one or more channels configured to transport the solution from the valve to the one or more sensors.

54. The cartridge of claim 50, wherein the flexible material defines a portion of the input channel such that the portion of the input channel defined by the flexible material has a volume that changes during operation of the valve.

55. The cartridge of claim 50, wherein a height of the input channel decreases moving toward the valve when the valve is closed, the height of the channel at a point along the channel being measured in a direction perpendicular to the flexible material and extending from the flexible material across the input channel to the point of the opposing side located furthest from the flexible material.

56. The cartridge of claim 50, wherein an opposite side of the vent channel from the flexible material slopes toward the flexible material.

57. The cartridge of claim 50, wherein a height of the vent channel decreases moving toward the valve when the valve is closed, the height of the channel at a point along the channel being measured in a direction perpendicular to the flexible material and extending from the flexible material across the channel to the point of the opposing side located furthest from the flexible material.

58. The cartridge of claim 50, wherein the transport component includes a cover positioned on a base, the cover and the base defining the input channel and defining the output channel, the base including:
   a first valve channel extending through the base and positioned over a portion of the input channel; and
   a second valve channel extending through the base and positioned over a portion of the output channel, the flexible material being positioned over the first valve channel and over the second valve channel.

59. A cartridge, comprising:
   a storage component including reservoirs that each contains a solution, the storage component including pockets extending from a side of a common platform, each pocket defining a portion of one of the reservoirs; and
   a transport component separate from the storage component and configured to be coupled with the storage component,
      the transport component being configured to transport the solutions from the reservoirs to a sensor held by the transport component, the sensor being configured to detect a presence and/or amount of an agent in a liquid sample, and
      the transport component includes disruption mechanisms configured to disrupt the sealing integrity of a material on the storage component upon coupling of the transport component and the storage component, the sealing integrity being disrupted so as to provide an outlet through which a solution in a reservoir can flow out of the storage component,
      one or more of the disruption mechanisms include a cup.

60. the cartridge of claim 59, wherein a lumen extends from the bottom of the cup into the transport component.

61. A cartridge, comprising:
   a storage component including reservoirs that each contains a solution, the storage component including pockets extending from a side of a common platform, each pocket defining a portion of one of the reservoirs; and
   a transport component separate from the storage component and configured to be coupled with the storage component,
      the transport component being configured to transport the solutions from the reservoirs to a sensor held by the transport component, the sensor being configured to detect a presence and/or amount of an agent in a liquid sample,
      the transport component including disruption mechanisms configured to disrupt the sealing integrity of a material on the storage component upon coupling of the transport component and the storage component, the sealing integrity being disrupted so as to provide an outlet through which a solution in a reservoir can flow out of the storage component, and
      one or more of the disruption mechanisms being configured to stretch the material upon coupling of the storage component and the transport component.

* * * * *